(12) United States Patent
McGahan et al.

(10) Patent No.: US 10,405,935 B2
(45) Date of Patent: Sep. 10, 2019

(54) SURGICAL IMPLANT BENDING SYSTEM AND METHOD

(71) Applicant: Warsaw Orthopedic, Inc, Warsaw, IN (US)

(72) Inventors: Thomas V. McGahan, Germantown, TN (US); Robert A. Till, Jr., Avon, IN (US); John Hengesbach, Carmel, IN (US); Richard L Brown, Mesa, AZ (US); Victor D. Snyder, Erie, CO (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/480,123

(22) Filed: Apr. 5, 2017

(65) Prior Publication Data

US 2018/0289396 A1 Oct. 11, 2018

(51) Int. Cl.
| | |
|---|---|
| A61B 17/70 | (2006.01) |
| A61B 34/37 | (2016.01) |
| A61B 34/20 | (2016.01) |
| A61B 34/00 | (2016.01) |
| A61B 17/88 | (2006.01) |

(52) U.S. Cl.
CPC .......... *A61B 34/37* (2016.02); *A61B 17/7011* (2013.01); *A61B 17/8863* (2013.01); *A61B 34/20* (2016.02); *A61B 34/25* (2016.02); *A61B 2034/2074* (2016.02)

(58) Field of Classification Search
CPC ................ A61B 17/7076–708; A61B 17/8863
See application file for complete search history.

(56) References Cited

U.S. PATENT DOCUMENTS

| | | | | |
|---|---|---|---|---|
| 5,490,409 A | * | 2/1996 | Weber ................ | A61B 17/8863 140/106 |
| 5,557,964 A | * | 9/1996 | Jessop ...................... | B21D 7/04 72/381 |
| 5,818,958 A | * | 10/1998 | Tomiyama ....... | G01N 21/95684 382/145 |
| 5,819,580 A | | 10/1998 | Gauthier | |
| 5,884,519 A | | 3/1999 | Theener | |
| 5,938,662 A | | 8/1999 | Rinner | |
| 6,035,691 A | * | 3/2000 | Lin .................... | A61B 17/8863 72/212 |
| 6,077,271 A | | 6/2000 | Huebner et al. | |
| 6,221,077 B1 | | 4/2001 | Rinner et al. | |
| 6,235,028 B1 | | 5/2001 | Brumfield et al. | |
| 6,298,706 B1 | | 10/2001 | Dunn | |
| 6,332,780 B1 | * | 12/2001 | Traxel ................ | A61B 17/7083 434/267 |
| 6,612,143 B1 | | 9/2003 | Butscher et al. | |
| 6,644,087 B1 | | 11/2003 | Ralph et al. | |
| 6,715,202 B2 | | 4/2004 | Beaver | |

(Continued)

*Primary Examiner* — Eduardo C Robert
*Assistant Examiner* — Michelle C Eckman

(57) ABSTRACT

A spinal implant system includes a spinal implant template having a base connected to vertebral tissue and a member movable relative to the base. The member includes a sensor configured to identify coordinates of one or more bone fasteners connected with the vertebral tissue. An implant bending device includes work surfaces engageable with a spinal implant to manipulate the spinal implant to a selected implant configuration based on the coordinates. Surgical instruments, spinal constructs, implants and methods are disclosed.

20 Claims, 37 Drawing Sheets

(56) References Cited

U.S. PATENT DOCUMENTS

| | | | |
|---|---|---|---|
| 6,732,558 B2 | 5/2004 | Butscher et al. | |
| 6,755,064 B2* | 6/2004 | Butscher | A61C 7/04 72/21.4 |
| 6,796,158 B2 | 9/2004 | Brzezniak et al. | |
| 6,854,311 B2 | 2/2005 | Schmauder et al. | |
| 6,860,132 B2 | 3/2005 | Butscher et al. | |
| 6,964,667 B2 | 11/2005 | Shaolian et al. | |
| 6,978,188 B1 | 12/2005 | Christensen | |
| 7,010,951 B2 | 3/2006 | Wang | |
| 7,013,547 B2 | 3/2006 | Lenzen et al. | |
| 7,024,901 B2 | 4/2006 | Yamaguchi et al. | |
| 7,076,980 B2 | 7/2006 | Butscher et al. | |
| 7,115,129 B2 | 10/2006 | Heggeness | |
| 7,283,891 B2 | 10/2007 | Butscher et al. | |
| 7,454,939 B2* | 11/2008 | Garner | A61B 17/8863 72/218 |
| 7,536,890 B2 | 5/2009 | Bulle | |
| 7,578,041 B2 | 8/2009 | Weber et al. | |
| 7,661,281 B2 | 2/2010 | Rubber et al. | |
| 7,742,801 B2 | 6/2010 | Neubauer et al. | |
| 7,837,467 B2 | 11/2010 | Butscher et al. | |
| 7,957,831 B2* | 6/2011 | Isaacs | A61B 17/7011 700/165 |
| 8,029,547 B2 | 10/2011 | Veldman et al. | |
| 8,082,769 B2 | 12/2011 | Butscher et al. | |
| 8,109,975 B2 | 2/2012 | Veldman et al. | |
| 8,118,840 B2 | 2/2012 | Trieu et al. | |
| 8,147,519 B2 | 4/2012 | Wilcox | |
| 8,177,843 B2 | 5/2012 | Schalliol | |
| 8,235,998 B2* | 8/2012 | Miller | A61B 17/8863 29/271 |
| 8,246,682 B2 | 8/2012 | Betz et al. | |
| 8,281,638 B2 | 10/2012 | Metzger | |
| 8,298,242 B2 | 10/2012 | Justis et al. | |
| 8,388,658 B2 | 3/2013 | Veldman et al. | |
| 8,459,090 B2 | 6/2013 | Wilcox et al. | |
| 8,495,901 B2 | 7/2013 | Hahn et al. | |
| 8,549,888 B2 | 10/2013 | Isaacs | |
| 8,573,019 B2* | 11/2013 | Steinhilber | B21F 1/00 700/165 |
| 8,607,603 B2* | 12/2013 | Justis | A61B 17/8863 140/123 |
| 8,631,674 B2 | 1/2014 | Christofillis et al. | |
| 8,646,300 B2* | 2/2014 | Caporusso | B21D 5/14 72/17.3 |
| 8,663,289 B2 | 3/2014 | Schwab | |
| 8,668,699 B2 | 3/2014 | Thomas et al. | |
| 8,677,793 B2 | 3/2014 | Spreitzer et al. | |
| 8,770,006 B2 | 7/2014 | Harper | |
| 8,781,557 B2 | 7/2014 | Dean et al. | |
| 8,935,974 B2* | 1/2015 | Crainich | A61B 17/8863 30/194 |
| 8,951,258 B2 | 2/2015 | Peultier et al. | |
| 8,989,460 B2 | 3/2015 | Mahfouz | |
| 9,003,859 B2 | 4/2015 | Paris et al. | |
| 9,014,835 B2 | 4/2015 | Azernikov et al. | |
| 9,017,386 B2 | 4/2015 | Rezach | |
| 9,044,285 B2 | 6/2015 | Harper | |
| 9,056,017 B2 | 6/2015 | Kotlus | |
| 9,101,405 B2 | 8/2015 | Dickinson et al. | |
| 9,208,558 B2 | 12/2015 | Dean et al. | |
| 9,250,620 B2 | 2/2016 | Kotlus | |
| 9,275,191 B2 | 3/2016 | Dean et al. | |
| 9,292,920 B2 | 3/2016 | Dean et al. | |
| 9,330,206 B2 | 3/2016 | Dean et al. | |
| 9,411,939 B2 | 8/2016 | Furrer et al. | |
| 9,414,859 B2 | 8/2016 | Ballard et al. | |
| 9,421,596 B2* | 8/2016 | Paris | B21F 1/002 |
| 9,474,582 B2 | 10/2016 | Musuvathy et al. | |
| 9,579,043 B2* | 2/2017 | Chien | A61B 5/742 |
| 9,848,922 B2* | 12/2017 | Tohmeh | A61B 17/7083 |
| 2003/0055435 A1* | 3/2003 | Barrick | A61B 5/1077 606/102 |
| 2005/0262911 A1* | 12/2005 | Dankowicz | B21D 7/14 72/31.04 |
| 2007/0227216 A1* | 10/2007 | Schalliol | B21D 7/12 72/31.04 |
| 2009/0249851 A1* | 10/2009 | Isaacs | A61B 17/7011 72/31.04 |
| 2011/0270262 A1* | 11/2011 | Justis | A61B 17/8863 606/101 |
| 2012/0186411 A1* | 7/2012 | Lodahi | B23D 15/02 83/452 |
| 2012/0247173 A1* | 10/2012 | Paris | A61B 17/8863 72/362 |
| 2014/0046372 A1* | 2/2014 | Ibrahim | A61B 17/7034 606/250 |
| 2014/0066994 A1* | 3/2014 | Dominik | B21D 7/063 606/281 |
| 2014/0100611 A1* | 4/2014 | Barry | A61B 17/7032 606/265 |
| 2014/0311203 A1* | 10/2014 | Crawford | B21D 7/08 72/129 |
| 2016/0262810 A1* | 9/2016 | Meyer | A61B 17/7076 |
| 2016/0263646 A1* | 9/2016 | Shazly | A61B 17/8863 |
| 2016/0346026 A1* | 12/2016 | Bootwala | A61B 17/8863 |
| 2016/0346027 A1* | 12/2016 | Rouge | B23D 21/08 |
| 2017/0325854 A1* | 11/2017 | Rouge | A61B 17/7074 |
| 2018/0280147 A1* | 10/2018 | McGahan | A61F 2/30942 |
| 2018/0289396 A1* | 10/2018 | McGahan | A61B 17/7013 |
| 2018/0289408 A1* | 10/2018 | McGahan | A61B 17/8863 |
| 2018/0289491 A1* | 10/2018 | McGahan | A61F 2/30942 |

* cited by examiner

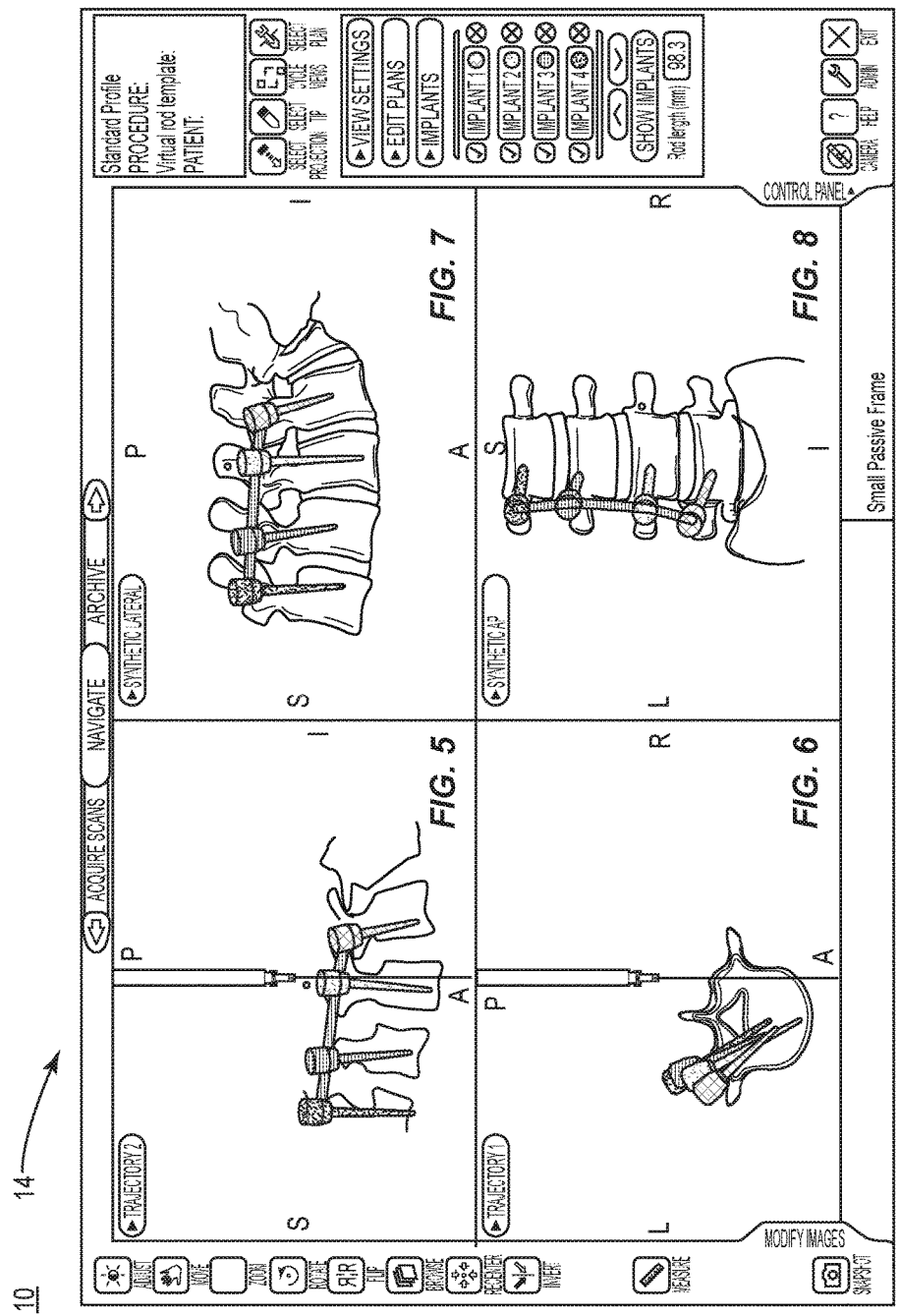

SURGICAL IMPLANT BENDING SYSTEM AND METHOD

TECHNICAL FIELD

The present disclosure generally relates to medical devices for the treatment of musculoskeletal disorders, and more particularly to a surgical system and a method, which employ one or more implants that may require bending for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods may require bending for disposal with the vertebral members. Such rods may be attached via fasteners to the exterior of two or more vertebral members. This disclosure describes an improvement over these prior technologies.

SUMMARY

In one embodiment, a spinal implant system is provided. The spinal implant system includes a spinal implant template having a base connected to vertebral tissue and a member movable relative to the base. The member includes a sensor configured to identify coordinates of one or more bone fasteners connected with the vertebral tissue. An implant bending device includes work surfaces engageable with a spinal implant to manipulate the spinal implant to a selected implant configuration based on the coordinates. In some embodiments, surgical instruments, spinal constructs, implants and methods are disclosed.

In one embodiment, a digitizer is provided. The digitizer includes a reference including a spheroidal joint connectable with a receiver of a bone fastener connected with a first vertebral level and a member including a sensor configured to intra-operatively identify coordinates of one or more bone fasteners connected with vertebral levels relative to the first vertebral level. The sensor communicates with a computer to display the coordinates from a graphical interface that provides implant indicia. An implant bending device includes work surfaces engageable with a spinal implant to manipulate the spinal implant to a selected implant configuration based on the coordinates.

In one embodiment, the spinal implant system includes a control device including a digitizer connected to a first vertebral level. The digitizer is configured to intra-operatively identify coordinates of one or more bone fasteners connected with vertebral levels relative to the first vertebral level. The digitizer communicates with a computer to display the coordinates from a graphical interface. A displacement module communicates with the control device and includes a movable support connectable with a spinal implant. A bending module communicates with the control device and includes work surfaces engageable with the spinal implant to manipulate the spinal implant to a selected implant configuration based on the coordinates.

BRIEF DESCRIPTION OF THE DRAWINGS

The present disclosure will become more readily apparent from the specific description accompanied by the following drawings, in which:

FIGS. 5, 6, 7, 8 are graphical representations of a computer showing components of one embodiment of a spinal implant system in accordance with the principles of the present disclosure;

DETAILED DESCRIPTION

Figure 1:
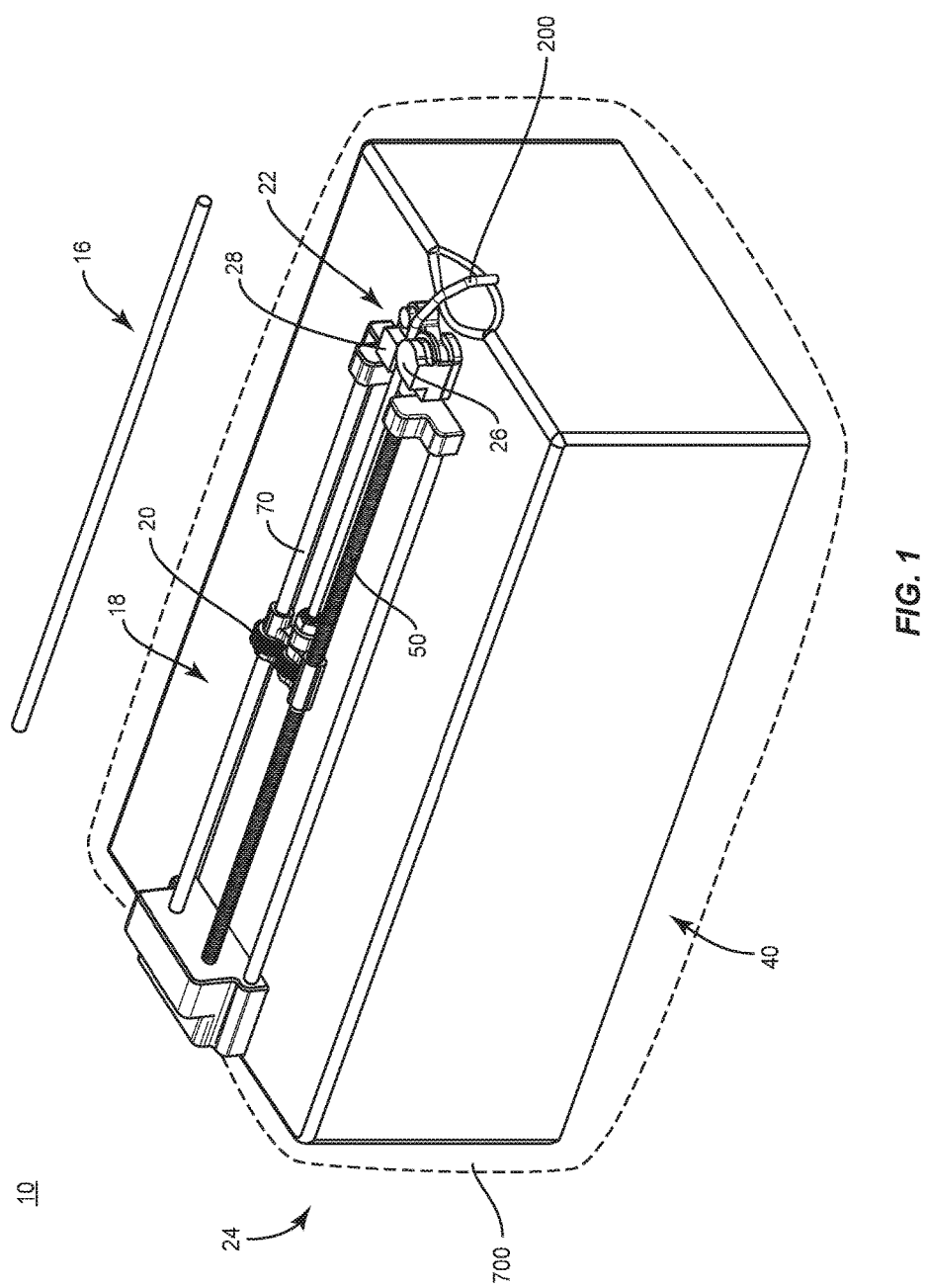
FIG. 1 is a perspective view of components of one embodiment of a spinal implant system in accordance with the principles of the present disclosure.

The exemplary embodiments of the surgical system and related methods of use disclosed are discussed in terms of medical devices for the treatment of musculoskeletal disorders and more particularly, in terms of a surgical system and method, which employ one or more implants that may require bending for treatment of a spine disorder. In some embodiments, the systems and methods of the present disclosure comprise medical devices including surgical instruments and implants that are employed with a surgical treatment, as described herein, for example, with a cervical, thoracic, lumbar and/or sacral region of a spine. See also, the examples and disclosure of systems and methods shown and described in commonly owned and assigned U.S. patent application Ser. No. 15/479,051 filed Apr. 4, 2017, and published as U.S. patent application Publication No. 20180280147, on Oct. 4, 2018; the examples and disclosure of systems and methods shown and described in commonly owned and assigned U.S. patent application Ser. No. 15/479,585 filed April 5, and published as U.S. patent application Publication No. 20180289408, on Oct. 11, 2018; and the examples and disclosure of systems and methods shown and described in commonly owned and assigned U.S. patent application Ser. No. 15/480,002 filed Apr. 5, 2017, and published as U.S. patent application Publication No. 20180289491, on Oct. 11, 2018, the entire contents of each of these disclosures being incorporated herein by reference.

In some embodiments, the present system comprises an automated, intra-operative implant bending device. In some embodiments, the implant bending device contours spinal rods for use with pedicle screws to form a corrective spinal construct. In some embodiments, the present system comprises an automated rod bender for extradiscal spine surgery. In some embodiments, the implant bending device is employed with spinal rods made from cobalt chrome alloys, stainless steel alloys, titanium alloys and/or having rod diameters of 6.0 millimeters (mm) or more.

In some embodiments, the present system comprises an implant bending device and a template, such as, for example, a soft rod that can be easily formed by a surgeon, in-situ, intra-operatively during the procedure and/or transferred from a sterile surgical field for analysis to define a selected spinal rod contour. In some embodiments, the template can include a three dimensional scanning device to provide a solid model of a spinal rod. In some embodiments, the model data is converted into machine code that allows the implant bending device, within the sterile field, to provide a surgery ready duplicate of the soft rod. In some embodiments, this configuration can be employed to duplicate a model rod in a two rod construct In some embodiments, the template includes surgical navigation to define a selected spinal rod contour. In some embodiments, the surgical navigation template includes a point-to-point definition of pedicle screw heads that can be utilized to define a spinal rod shape. In some embodiments, the initial definition can be manipulated via surgeon preference for additional corrective needs of the patient during the surgical procedure. In some embodiments, the surgical navigation template could be utilized to smooth contours initially defined.

In some embodiments, the template includes a digitizing arm. In some embodiments, the template includes a disposable, single use, digitizing arm. In some embodiments, the digitizing arm defines data points, which can be converted into a three dimensional model that is translated into machine code and communicated to the automated bender. In some embodiments, the digitizing arm includes a reference and/or a base directly connected to a pedicle screw attached with vertebrae. In some embodiments, the template includes a digitizing arm and an adaptor that connects a base of the digitizing arm to the pedicle screw. In some embodiments, connection of the digitizing arm directly to a bone screw attached with vertebrae provides a shorter distance between a base of the digitizing arm and selected data points, such as, for example, receivers and/or screw heads of one or a plurality of bone screws.

In some embodiments, the template includes computer generated models of rod configurations having a selected curvature such that the selected rod configurations are produced by the automated bender and packaged sterile. In some embodiments, the selected rod configurations could be stored in a variety of locations, including the hospital. In some embodiments, the selected rod configurations can be employed with pre-operative planning including initiatives to plan screw locations and the corresponding rods needed for correction.

In some embodiments, the present system comprises an implant bending device utilized in a sterile field. In some embodiments, the implant bending device includes a boxed container for disposal of one or more components of the system. In some embodiments, the implant bending device includes drive sockets that are covered with a sterile drape. In some embodiments, the implant bending device includes a drive plate for forming the spinal rod that is autoclaved and placed upon the sterile drape. In some embodiments, the implant bending device includes drive posts that extend from a top plate and perforate the drape and connect to the drive sockets within the boxed container. In some embodiments, the implant bending device is employed with a method for scoliosis surgery and degenerative length rods. In some embodiments, the implant bending device includes a cube version that allows a surgeon to insert the rod into the implant bending device and sequentially provide contour to the rod.

In some embodiments, the implant bending device is employed with a template that includes one or more of digitizing arms, three dimensional scanners, orthogonal camera technology, surgical navigation, soft rod in situ, pre-bent configurations and various forms of preoperative planning initiatives. In some embodiments, the implant bending device includes a drive mechanism contained in an enclosure, which includes drive sockets on a top surface and is disinfected and sterile draped. In some embodiments, the implant bending device includes a drive and bending device disposed on a stand-alone plate that is autoclaved. In some embodiments, the drive and bending plate has drive posts that perforate the sterile drape while at the same time sealing the sterile field from the drive enclosure. In some embodiments, the implant bending device is connected with data storage for storing one or more spinal rod geometries, for example, in a patient record. In some embodiments, the data storage can include lordosis angles and sagittal balance criteria correlated to rod definition. In some embodiments, the data storage provides data for spine studies to determine rod profile vs. post-op correction achieved.

In some embodiments, the present system comprises an implant bending device utilized in a sterile field and including a base unit drive enclosure, a drive and bending mechanism including a rod transport unit with drive posts and a sterile drape. In some embodiments, the drive and bending mechanism includes a rod bending head.

In some embodiments, the present system comprises an automated implant bending device, a rod template and three dimensional rod coordinates of a selected rod configuration such that the implant bending device forms a spinal rod having the selected rod configuration. In some embodiments, the present system comprises an automated implant bending device that includes a control device having a displacement module and a bending module, and a spinal rod. In some embodiments, the bending module includes a linear actuator. In some embodiments, the linear actuator has a force capacity of 680 Newtons (N). In some embodiments, the bending module has a torque application capacity of one or more values in a range of 70-85 Newton-meters (N-m) on a spinal rod. In some embodiments, the displacement module includes a stepper motor and a gear transmission for translating a spinal rod. In some embodiments, the displacement module includes a stepper motor and a mandrel for rotating a spinal rod.

In some embodiments, the present system comprises an automated implant bending device that includes a computer having a graphical interface, processor and storage media for storage of template and/or spinal rod data. In some embodiments, the graphical interface provides indicia of template and/or spinal rod data including file information, rod diameter, rod material, bending status, bending progress, control points and/or three dimensional graphical representation of rod formation. In some embodiments, the automated implant bending device includes one or more sensors that communicate with the computer and/or graphical interface to provide rod curvature, which may include a geometric angle between two consecutive points on a spinal rod, bending angle, which may include elastic spring back of the spinal rod and/or tension/position. In some embodiments, the implant bending device allows a maximum bend angle before rod spring back of 50 angular degrees. In some embodiments, the implant bending device allows a maximum bend angle after rod spring back of less than 50 angular degrees. In some embodiments, the implant bending device performs rod bending with an accuracy for rotation of a spinal rod of ±3 angular degrees. In some embodiments, the implant bending device performs rod bending for translation displacement of a spinal rod with an accuracy of ±3 mm. In some embodiments, the implant bending device performs rod bending for a bending angle of a spinal rod with an accuracy of ±1 angular degree. In some embodiments, the implant bending device performs intra-operative rod bending in a duration of less than five minutes. In some embodiments, the implant bending device performs rod bending for 4.5, 4.75, 5.5, 6.0 and/or 6.35 mm spinal rod diameters.

In some embodiments, the implant bending device comprises a base unit with an actuator motor, for example, a stepper motor having a drive with a spiral bevel gear engageable with a spiral bevel gear of an output shaft. In some embodiments, the output shaft has a spline surface. In some embodiments, the implant bending device comprises a bending head having at least one bending arm. In some embodiments, the output shaft is connected with the bending head.

In some embodiments, the implant bending device comprises an engagement detector disposed with the bending head. In some embodiments, the engagement detector provides data and/or indicia of non-contact with a spinal rod and engagement with the spinal rod. In some embodiments, the implant bending device comprises a contact/non-contact measuring device for rod bending. In some embodiments, the implant bending device comprises an engagement detector that senses spinal rod spring-back after a spinal rod is bent to a desired angle. In some embodiments, the engagement detector includes an electromechanical mechanism that can determine when a bending arm of the implant bending device makes initial contact with the rod, or breaks contact with the rod after a bend. In some embodiments, the engagement detector provides feedback to define angular relationships and provides the ability to adjust a bending cycle to yield a selected bend output. In some embodiments, the engagement detector allows for adjustment of angular relationships in real time and/or during an intra-operative bending procedure.

In some embodiments, the implant bending device comprises an engagement detector having one or more elements, such as, for example, two thin optical discs that contain etched, circular, interference patterns. In some embodiments, the engagement detector includes at least one disc that is mounted, on-axis, to the rotation of a bending arm of the implant bending device. In some embodiments, the engagement detector includes at least one disc that is mounted, on-axis, to a spring loaded clutch on a motor drive of the implant bending device. In some embodiments, as the bending arm approaches the rod, both discs are aligned such that the interference patter of the discs is disposed in an open configuration. As the bending arm contacts the rod, the initial contact bending force engages a clutch of the engagement detector and creates a difference in the interference pattern such that the discs are oriented out of alignment and disposed in a closed configuration. In some embodiments, the pattern created by the discs is sensed and/or viewed by a sensor. In some embodiments, the engagement detector is activated by a change in the disc pattern when bending starts and when bending ends.

In some embodiments, the engagement detector allows the implant bending device to define angular measurements based on the engagement detector reading touch-on and touch-off positions of the bending arm relative to the rod. In some embodiments, the engagement detector allows the implant bending device to detect and record angular measurement for touch and release points for real time angular adjustments. In some embodiments, the implant bending device employs the engagement detector to sense angular measurement and adjust to a defined angle, in real time and/or intra-operatively, and can address spring back, rod diameter and rod inconsistencies. In some embodiments, the engagement detector provides detection sensing capability, which could be utilized to bend scoliosis configurations intra-operatively.

In some embodiments, the engagement detector includes a torsion spring connected with discs mounted with the bending head. The discs include alignable openings and are relatively movable for passage or blocking of light detectable by a sensor. In some embodiments, the discs are disposed and/or relatively rotatable to dispose the openings in an aligned orientation when the bending head and a spinal rod are in a non-contacting relation. In the non-contacting orientation of the bending head and the spinal rod, a sensor detects light emitted through the aligned orientation of the openings and transmits a signal, as described herein, to provide data and/or indicia of non-contact of the bending head with the spinal rod. In some embodiments, the discs are disposed and/or relatively rotatable to dispose the openings in a non-aligned orientation when the bending head and the spinal rod are in an engaging relation. In the engaging orientation of the bending head and the spinal rod, the openings are not aligned and block transmission of light such that the sensor cannot detect the emitted light and transmits a signal, as described herein, to provide data and/or indicia of engagement of the bending head with the spinal rod.

In some embodiments, the bending head is rotated in increments, for example, increments of 0.5 angular degrees to determine or sense an initial contact point or engagement of the bending head with a spinal rod, which can represent a "0" degree reference position. For example, if a selected rod curvature includes a 35 degree bend, the bending head rotates 35 degrees in a first direction and engages the spinal rod to effect a 35 degree bend. The bending head is then rotated in a second opposite direction in increments, for example, of 0.5 angular degrees to disengage the bending head from the spinal rod. When the bending head no longer has contact with the spinal rod as detected by the engagement detector, the resulting bend formed in the spinal rod is measured based on the bending head position and/or angle relative to the reference position. The difference between the resulting bend angle and the selected rod curvature of 35 degrees represents spring back, which can include a delta angle measured by the bending head position. In some embodiments, the data and/or indicia from sensors of the implant bending device is displayed from a computer and/or graphical interface, as described herein. In some embodiments, the engagement detector can be employed with or create a lookup table of spinal rod data, as described herein, to facilitate compensation for spring back. In some embodiments, the engagement detector can be employed with a method including the steps of bending a spinal rod to a selected rod curvature, measuring spring back and bending the spinal rod to a new angle with spring back compensation.

In some embodiments, the engagement detector includes a contact/non-contact clutch. In some embodiments, the contact/non-contact clutch includes interference discs connected with a torsion spring that facilitates relative rotation of the discs. In some embodiments, the discs are disposed with a coupler connected with a drive shaft of the implant bending device. In some embodiments, the discs are connected with a light emitter/detector. In some embodiments, the implant bending device includes sensors.

In some embodiments, the present system acquires digital measurements that represent shape data of a spinal rod template representing a final rod to be implanted with a patient. In some embodiments, the spinal rod template is manually formable. In some embodiments, the spinal rod template has a shape sensor to sense a shape of the template. In some embodiments, a controller receives template shape data from the shape sensor and operates the bending machine to effect a selected curvature with a spinal rod. In some embodiments, the present system includes a sensor, processor, computer and a bending arm that compensate for rod spring back during an intra-operative bending procedure, and which can be employed with template shape data.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and iliac regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical bending device, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-41, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, superelastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 41:
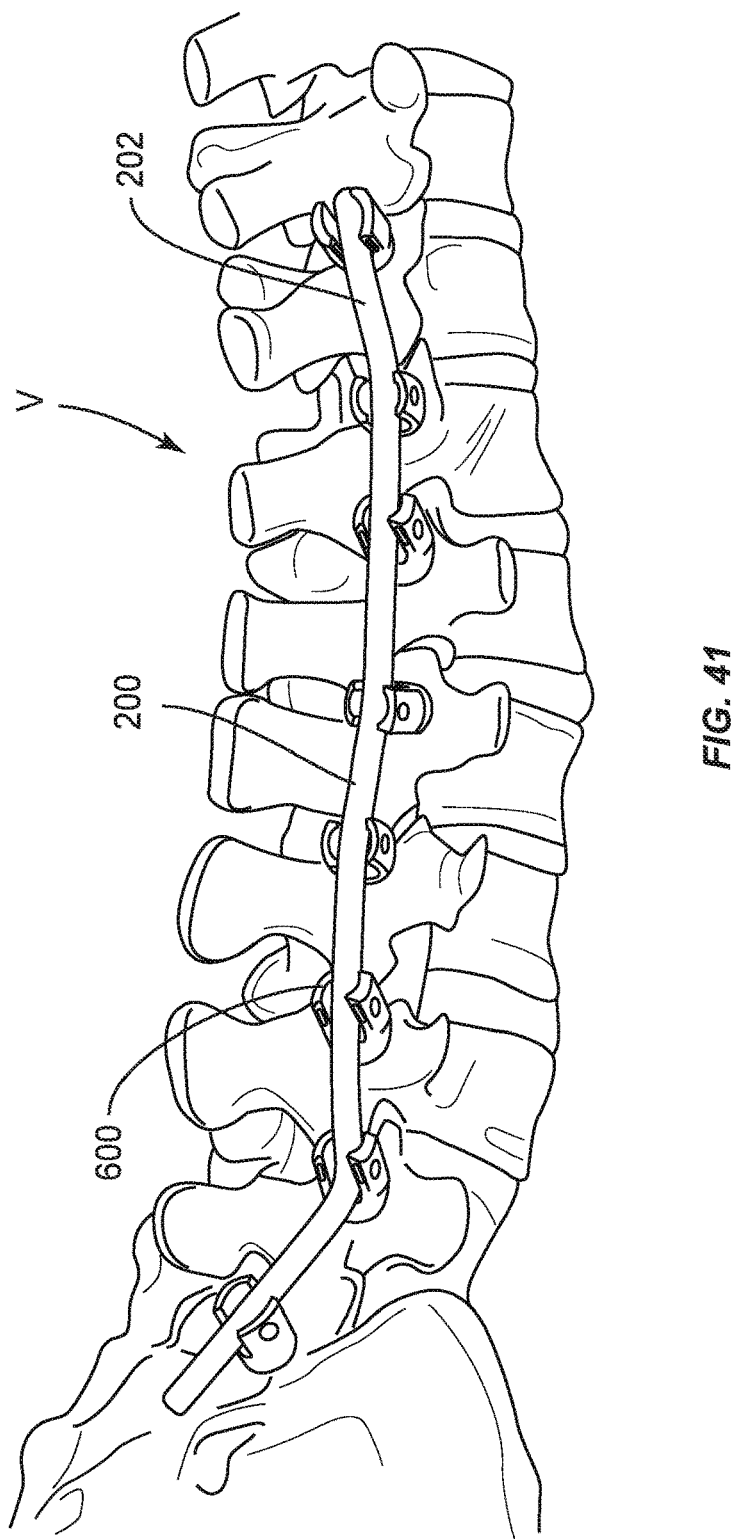
FIG. 41 is a perspective view of components of one embodiment of a spinal implant system in accordance with the principles of the present disclosure disposed with vertebrae.

Spinal implant system 10 comprises an automated, intra-operative system configured to contour spinal implants, such as, for example, a spinal rod 200 with pedicle screws to form a corrective spinal construct 202 (FIG. 41). In some embodiments, spinal implant system 10 comprises an automated implant system for extradiscal spine surgery. In some embodiments, spinal implant system 10 is employed with spinal rod 200 fabricated from cobalt chrome and/or having rod diameters of 6.0 mm or more.

Figure 2:
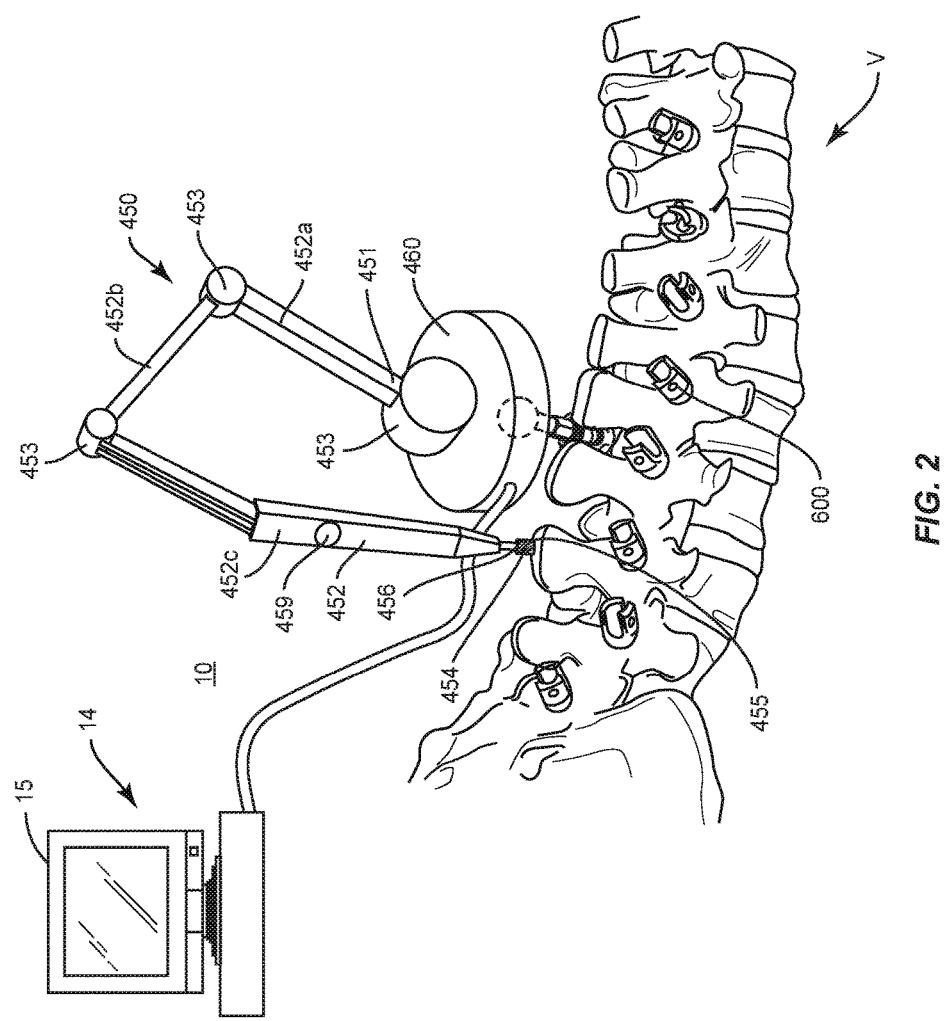
FIG. 2 is a perspective view of components of one embodiment of a spinal implant system in accordance with the principles of the present disclosure.

Spinal implant system 10 includes a control device having a computer 14 (for example, as shown in FIG. 2). In one embodiment, computer 14 receives data from a template, such as, for example, a soft rod 16, as shown in FIG. 1. Rod 16 is flexible, bendable and/or malleable and can be formed in-situ, intra-operatively during the procedure and/or transferred from a sterile surgical field for analysis to define a selected spinal rod contour or configuration. For example, a formed rod 16 having a selected implant configuration can be scanned with a three dimensional scanning device, as described herein, to generate three dimensional coordinates of the selected implant configuration of formed rod 16. The coordinates of the selected implant configuration are communicated to computer 14 and transferred to an implant bending device 24 and/or displayed from a graphical interface, as described herein and for example, a monitor 15 (FIG. 2).

In some embodiments, the template can include a three dimensional scanning device to provide a solid model of a spinal rod 200. In some embodiments, the model data is communicated to computer 14 and/or displayed from a graphical interface, as described herein, and converted into computer readable machine code. Computer 14 communicates a corresponding signal to implant bending device 24, within a sterile field, to contour spinal rod 200 and provide a surgery ready duplicate of rod 16. In some embodiments, implant bending device 24 is connected with computer 14 and data storage for storing one or more spinal rod 200 geometries, for example, in a patient record, pre-bent configurations and various forms of preoperative planning initiatives. In some embodiments, the data storage can include lordosis angles and sagittal balance criteria correlated to spinal rod 200 shape. In some embodiments, the data storage provides data for spine studies to determine spinal rod 200 profile vs. post-op correction achieved.

Rod 16 is manually shaped to a selected implant configuration by disposing rod 16 in-situ. In some embodiments, rod 16 has a shape sensor (not shown) to sense a shape of rod 16. In some embodiments, computer 14 receives rod 16 shape data from the shape sensor and operates implant bending device 24 to effect a selected curvature of spinal rod 200, as described herein. In some embodiments, rod 16 includes a manually formable link construction.

Figure 3:
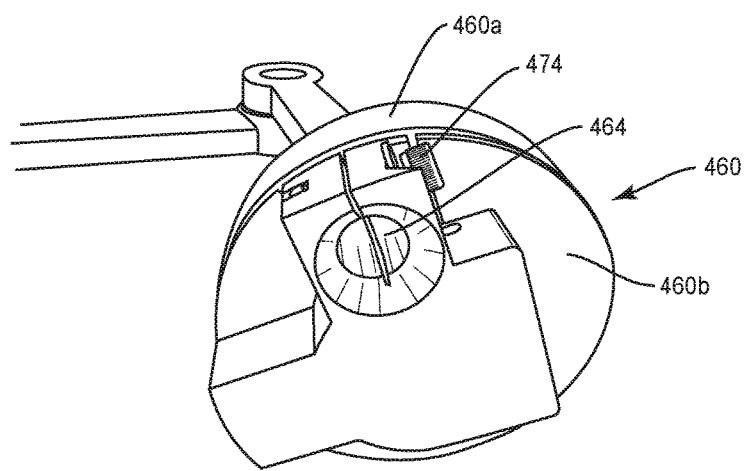
FIG. 3 is a perspective view of components of one embodiment of a spinal implant system in accordance with the principles of the present disclosure.
Figure 4:
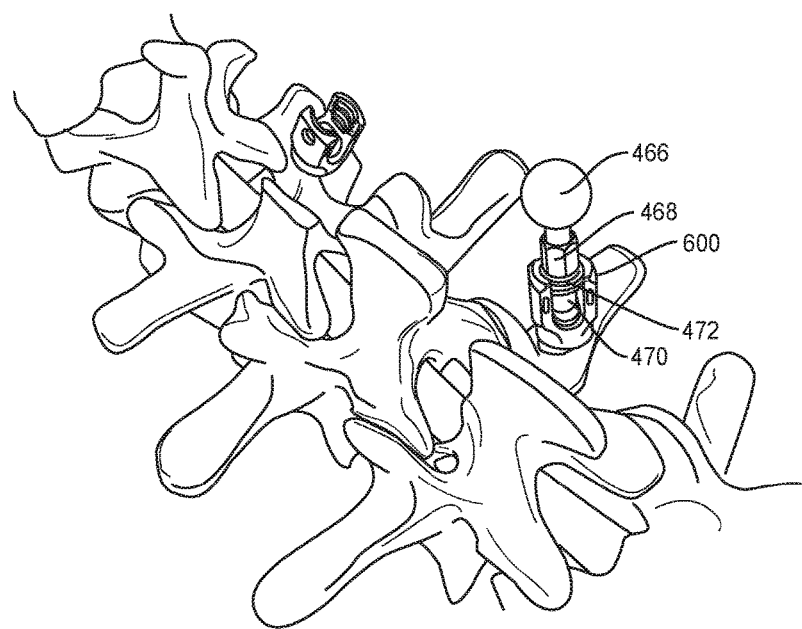
FIG. 4 is a perspective view of components of one embodiment of a spinal implant system in accordance with the principles of the present disclosure disposed with vertebrae.
Figure 9:
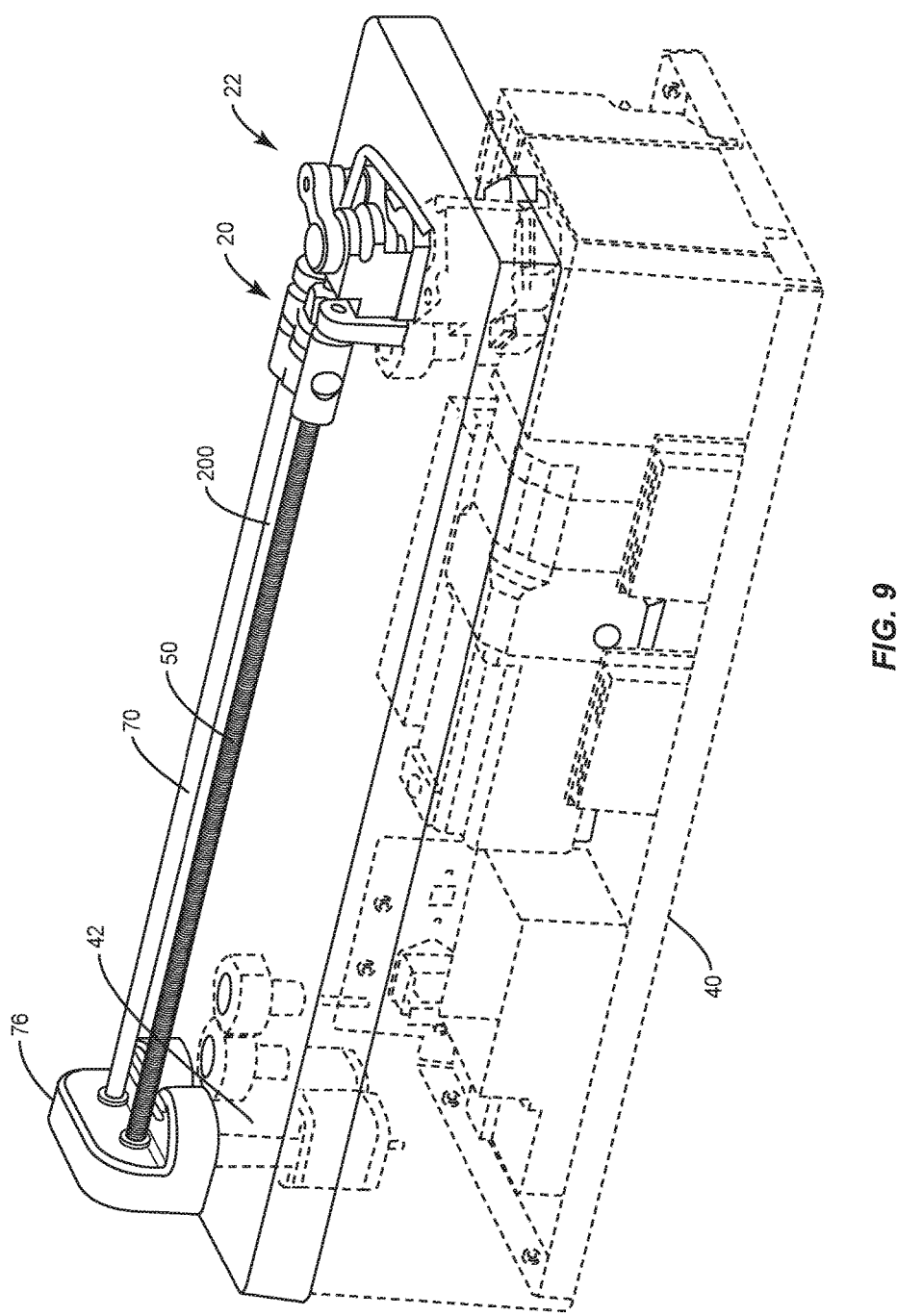
FIG. 9 is a perspective view, in part phantom, of components of one embodiment of a spinal implant system in accordance with the principles of the present disclosure.

In one embodiment, as shown in FIGS. 2-4, the template, similar to that described herein, includes a digitizer 450 that is directly connected to a bone screw attached with vertebrae to capture and/or identify selected data points corresponding to receivers of one or a plurality of bone screws to generate three dimensional coordinates of a selected implant configuration. Digitizer 450 defines such data points, which are converted into a three dimensional model of spinal rod 200 that is translated into machine code and communicated to implant bending device 24, as described herein.

Digitizer 450 includes a member, such as, for example, an articulating arm 452. Arm 452 extends between an end 451 and an end 455. End 451 is connected with a base 460 via a pivot joint 457 such that arm 452 extends from base 460 and is rotatable relative to base 460 in one or a plurality of axial orientations. Base 460 has a circular disc shape and provides communication and/or electrical connection of digitizer 450 with computer 14, similar to that described herein. In some embodiments, digitizer 450 can communicate with computer 14 in a wired and/or wireless connection, similar to that described herein.

Base 460 is configured for connection with a receiver 602 of bone fastener 600 attached with a selected vertebral level V1 to provide a reference for intra-operative identification of coordinates of one or more bone fasteners 600 connected with vertebral levels relative to vertebral level V1. Base 460 includes a part, such as, for example, a disc 460a and a part, such as, for example, a disc 460b, as shown in FIG. 3. Disc 460a is configured for rotation relative to disc 460b. A position sensor (not shown), similar to those described herein, is disposed between discs 460a, 460b and configured to capture rotational coordinates of arm 452 relative to disc 460b, bone fastener 600 disposed at vertebral level V1 and/or vertebrae V in a horizontal plane defined between discs 460a, 460b.

Disc 460b includes a spheroidal joint 462 that facilitates adjustable connection of digitizer 450 with bone fastener 600 disposed at vertebral level V1. Disc 460b includes a bi-furcated clamp surface that defines a socket 464 configured for disposal of a ball 466. Ball 466 and socket 464 form spheroidal joint 462 to facilitate adjustable connection of base 460 with bone fastener 600 disposed at vertebral level V1. As such, disc 460b is fixed with bone fastener 600 and disc 460a is moveable relative to bone fastener 600 disposed at vertebral level V1 and/or vertebrae V in one or a plurality of axial orientations to facilitate positioning of base 460 with bone fastener 600 disposed at vertebral level V1.

Ball 466 includes a post 468 that includes an end 470 configured for engagement with receiver 602. End 470 includes a threaded surface 472 configured for engagement with a threaded inner surface of receiver 602 to fix post 468 with bone fastener 600. The bi-furcated clamp surface of base 460 includes an inner threaded cavity engageable with a lock screw 474. Upon disposal of base 460 in a selected orientation relative to bone fastener 600 disposed at vertebral level V1 and/or vertebrae V, lock screw 474 engages base 460 and draws the clamp surfaces together to fix the selected orientation of base 460 relative to bone fastener 600 disposed at vertebral level V1 and/or vertebrae V.

Arm 452 includes one or a plurality of extensions, such as, for example, extensions 452a, 452b, 452c. Extensions 452a, 452b, 452c are connected by joints 453 to facilitate pivotal and/or rotational movement of extensions 452a, 452b, 452c relative to each other, base 460 and/or vertebrae V. Extensions 452a, 452b, 452c facilitate articulation of arm 452 into engagement with one or more bone fasteners 600 disposed with vertebrae V to capture and/or identify selected data points corresponding to receivers 602 and/or a selected curvature of spinal rod 200, as described herein. In some embodiments, the member of digitizer 450 comprises a tether. In some embodiments, arm 452 includes a push button actuator 459 configured to actuate measurement, sample, capture and/or identification of positional data points of end effector 456 in three dimensional space, for example, upon selective positioning of tip 454 engaged with bone fastener 600.

End 455 includes a tip 454 having a spherical end effector 456. Joints 453, 457 of arm 452 include position sensors (not shown) that measure, sample, capture and/or identify positional data points of end effector 456 in three dimensional space corresponding to receivers 602 attached with selected vertebral levels of vertebrae V relative to bone fastener 600 disposed at vertebral level V1. The position sensors are mounted with each of joints 453 and joint 457 and calibrated to measure positional data points of end effector 456 in three dimensional space, which are communicated to computer 14, as described herein. In some embodiments, position sensors can be mounted with only one, a plurality or all of joints 453, 457. In some embodiments, end effector 456 can include a cylindrical configuration.

Figure 37:
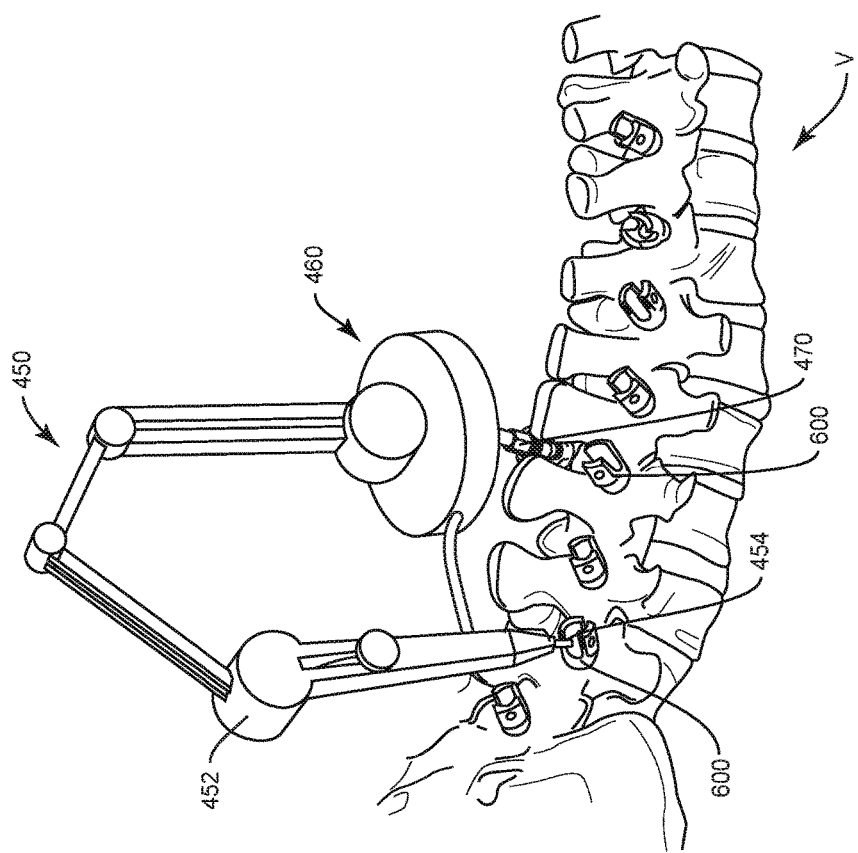
FIG. 37 is a perspective view of components of one embodiment of a spinal implant system in accordance with the principles of the present disclosure disposed with vertebrae.
Figure 38:
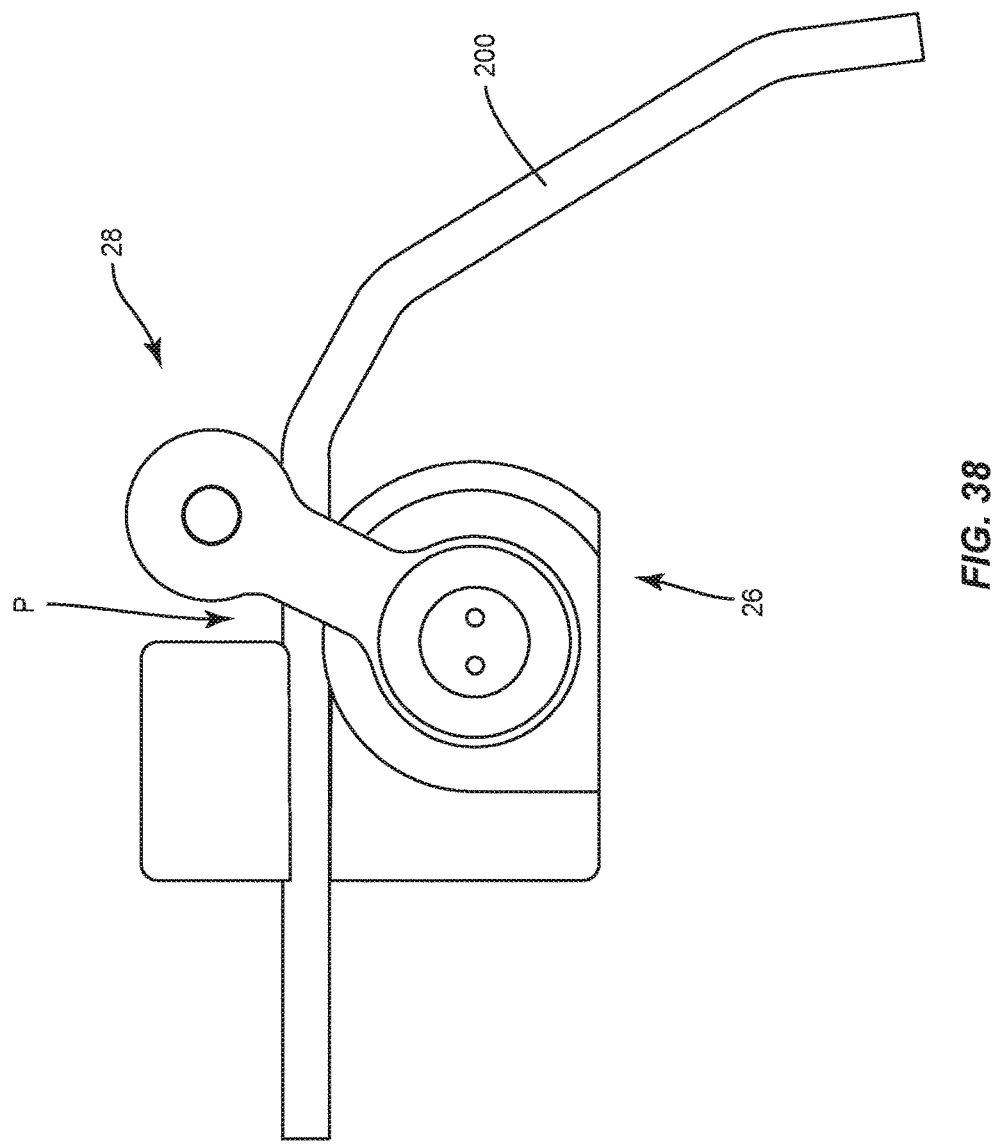
FIG. 38 is a top view of components of one embodiment of a spinal implant system in accordance with the principles of the present disclosure.
Figure 39:
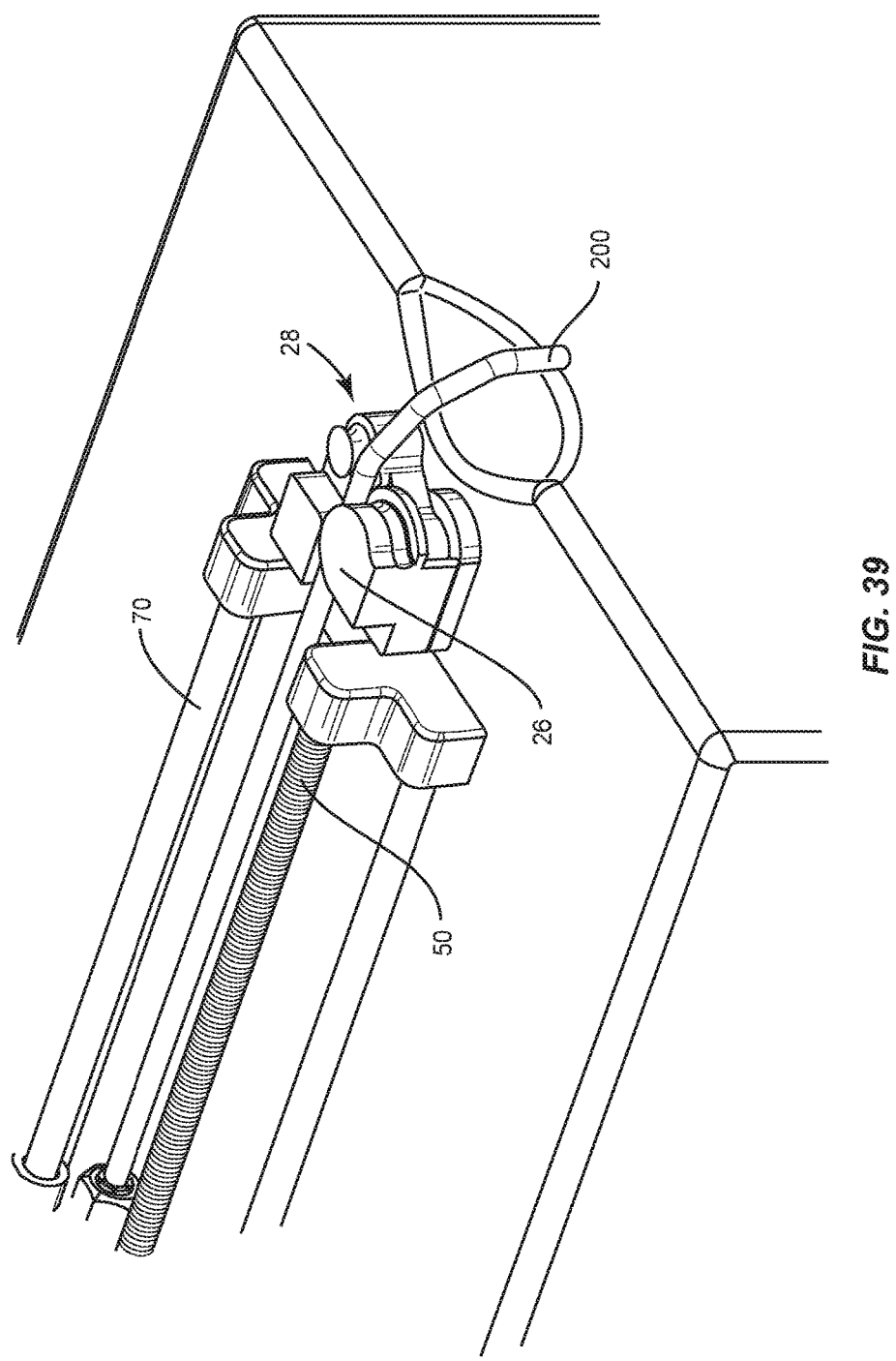
FIG. 39 is a perspective view of components of one embodiment of a spinal implant system in accordance with the principles of the present disclosure.
Figure 40:
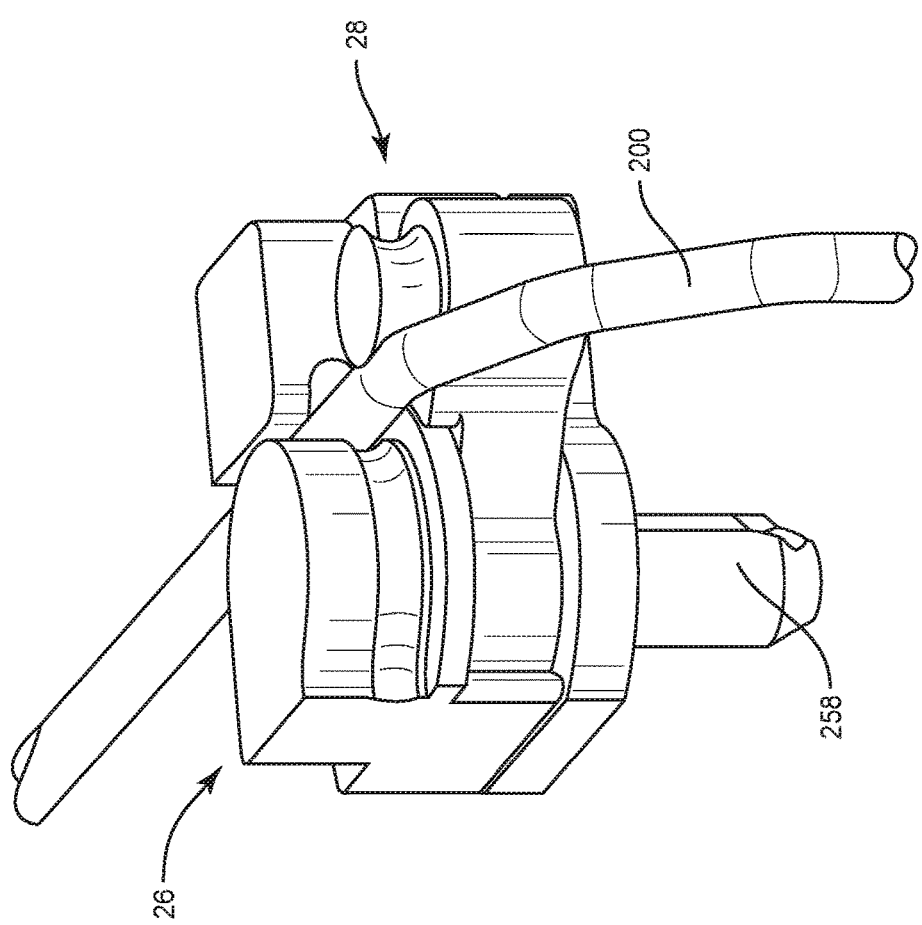
FIG. 40 is a perspective view of components of one embodiment of a spinal implant system in accordance with the principles of the present disclosure.

Articulation of arm 452 orients tip 454 and end effector 456 for engagement with receivers 602 relative to one or more extensions, base 460 and/or vertebrae V. Tip 454 is engageable with one or more receivers 602 such that end effector 456 is disposable adjacent, within, on or about each receiver 602. As such, the position sensors of discs 460a, 460b, and joints 453, 457 intra-operatively measure, sample, capture and/or identify selected positional data points of end effector 456 in three dimensional space corresponding to receivers 602, for example, corresponding to positioning of bone fasteners 600 to determine a selected spinal rod curvature at various vertebral levels along vertebrae V (FIG. 37). In some embodiments, end effector 456 is configured for engagement with variously configured receivers and/or bone fasteners, such as, for example, sagittal angulation screws, pedicle screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, connectors, fixation plates and/or posts. In some embodiments, end effector 456 is configured to translate and/or pass through receiver 602 and engage a female opening and/or socket, such as, for example, a hexagonal, torx, rectangular, polygonal or oval shaped opening in a head of a shaft of bone fastener 600. In some embodiments, linear contact between tip 454 of arm 452 and the opening or socket of bone fastener 600 provides an angular trajectory of an axis along a length of bone fastener 600 fixed with tissue, which data can be stored with computer 14, as described herein.

The data points include three dimensional coordinates of a selected spinal rod configuration, which are communicated to computer 14 and converted into a three dimensional model of spinal rod 200. The three dimensional model of spinal rod 200 is translated into machine code and communicated to implant bending device 24 within a sterile field to contour spinal rod 200 and/or produce a digitized image displayed from monitor 15, as described herein. See, for example, the sensors and sensing systems disclosed in U.S. Pat. No. 8,177,843, the contents of which being incorporated by reference herein. In some embodiments, the position sensors of digitizer 450 can include one or more potentiometer and/or variable resistor sensors, that measure, sample, capture and/or identify positional data points of end effector 456 in three dimensional space. See, for example, position sensors manufactured by Bourns, Inc., for example, position sensor-Model No. 3382-12 mm. In some embodiments, the potentiometer and/or variable resistor sensors can include angle sensors, linear sensors and/or tilt angle sensors. In some embodiments, the position sensors of digitizer 450 can include one or more two-dimensional or three-dimensional digital position sensors and/or three-axis magnetic force sensors.

In one embodiment, the template includes a surgical navigation system that generates the three dimensional coordinates of a selected implant configuration in connection with computer 14 for display from a graphical interface, as shown in FIGS. 5-8, and communicates the coordinates to implant bending device 24 within a sterile field, to contour spinal rod 200, as described herein. The surgical navigation system employs a surgical instrument and the graphical interface(s) to acquire data and generate a signal representative of a position of one or more surfaces of vertebrae V and/or components of spinal construct 202. See, for example, similar surgical navigation components and their use as described in U.S. Pat. Nos. 6,021,343, 6,725,080, 6,796,988, the entire contents of each of these references being incorporated by reference herein.

The surgical navigation system acquires the data and displays medical imaging to generate the three dimensional coordinates of the shape of spinal rod 200 with computer 14. The surgical navigation system can include those components disclosed in U.S. Pat. Nos. 8,842,893, 7,188,998; 7,108,421; 7,106,825; 7,001,045; and 6,940,941; the entire contents of each of these references being incorporated by reference herein. The surgical navigation system can include a tracking system in connection with acquiring the data. In some embodiments, the tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein. In some embodiments, fluoroscopic images taken are transmitted to computer 14. Image transfer may be performed over a standard video connection or a digital link including wired and wireless. Computer 14 and/or the graphical interface, as described herein, provides the ability to display, via a monitor, as well as save, digitally manipulate, or print a hard copy of the received images. In some embodiments, images may also be displayed to the surgeon through a heads-up display.

In some embodiments, the graphical interface, as described herein, provides indicia of template or spinal rod data including file information, diameter of spinal rod 200, material of spinal rod 200, bending status, bending progress, control points and/or three dimensional graphical representation of spinal rod 200 formation. In some embodiments, implant bending device 24 communicates with computer 14 and/or the graphical interface to provide the curvature coordinates of spinal rod 200, which may include a geometric angle between two consecutive points on spinal rod 200, bending angle, which may include elastic spring back of spinal rod 200 and/or tension/position. In some embodiments, implant bending device 24 allows a maximum bend angle before spinal rod 200 spring back of 50 angular degrees. In some embodiments, implant bending device 24 allows a maximum bend angle after spinal rod 200 spring back of less than 50 angular degrees. In some embodiments, implant bending device 24 performs spinal rod 200 bending with an accuracy of ±3 angular degrees. In some embodiments, implant bending device 24 performs rod bending for translation displacement of spinal rod 200 with an accuracy of ±3 mm. In some embodiments, implant bending device 24 performs spinal rod 200 bending for bending angle of spinal rod 200 with an accuracy of ±1 angular degree. In some embodiments, implant bending device 24 performs intraoperative spinal rod 200 bending in a duration of less than five minutes. In some embodiments, implant bending device 24 performs spinal rod 200 bending for 4.5, 4.75, 5.5, 6.0 and/or 6.35 mm diameters.

Implant bending device 24, as shown in FIGS. 9-13, includes a base, such as, for example, a boxed container 40 for disposal of one or more components of spinal implant system 10. Implant bending device 24 includes a displacement module 18 and a bending module 22. Displacement module 18 includes a movable support, such as, for example, a carrier 20 that communicates with computer 14, as described herein. Carrier 20 is configured to support spinal rod 200 during translation and/or rotation, as described herein.

Bending module 22 includes work surfaces, such as, for example, a mandrel 26 and an arm 28, and a contact sensor 30 (FIG. 26), as described herein. Bending module 22 communicates with computer 14 and is engageable with spinal rod 200 to manipulate spinal rod 200 to a selected implant configuration, as described herein. In some embodiments, implant bending device 24 is employed with a method for scoliosis surgery. In some embodiments, implant bending device 24 is employed with a method of implanting degenerative length spinal rods 200.

Figure 10:
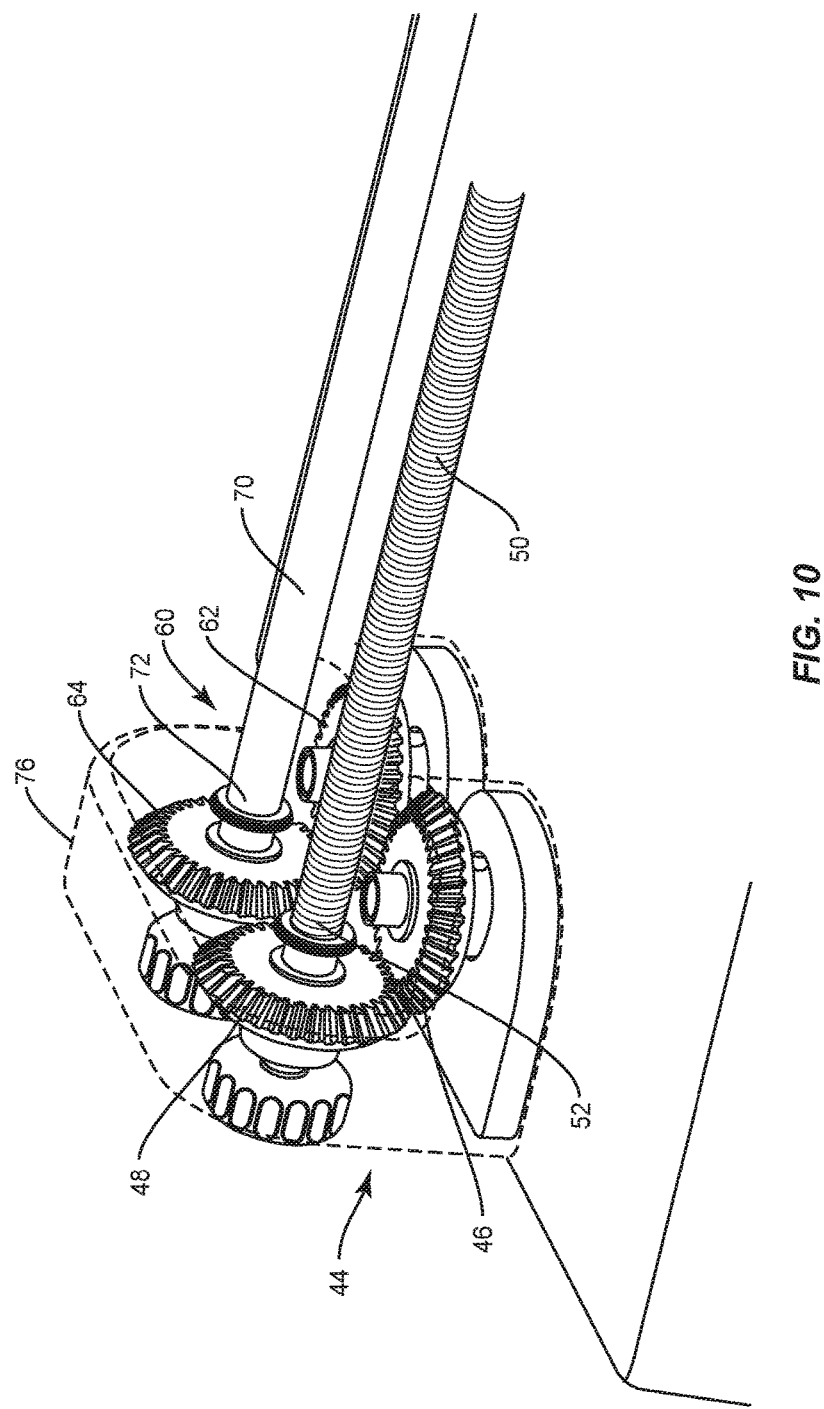
FIG. 10 is a break away view, in part phantom, of the components shown in FIG. 1.
Figure 11:
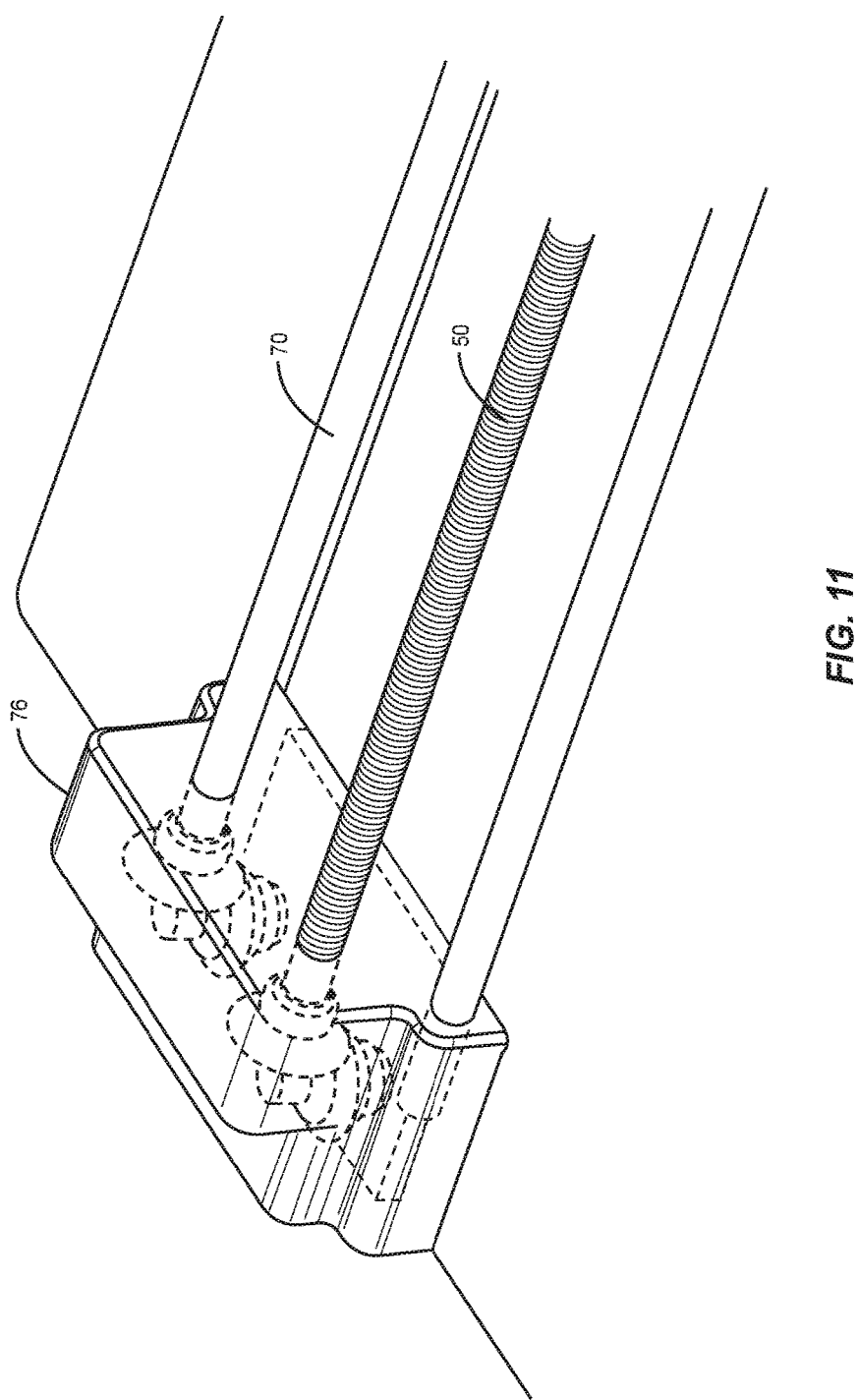
FIG. 11 is a break away view, in part phantom, of the components shown in FIG. 1.
Figure 12:
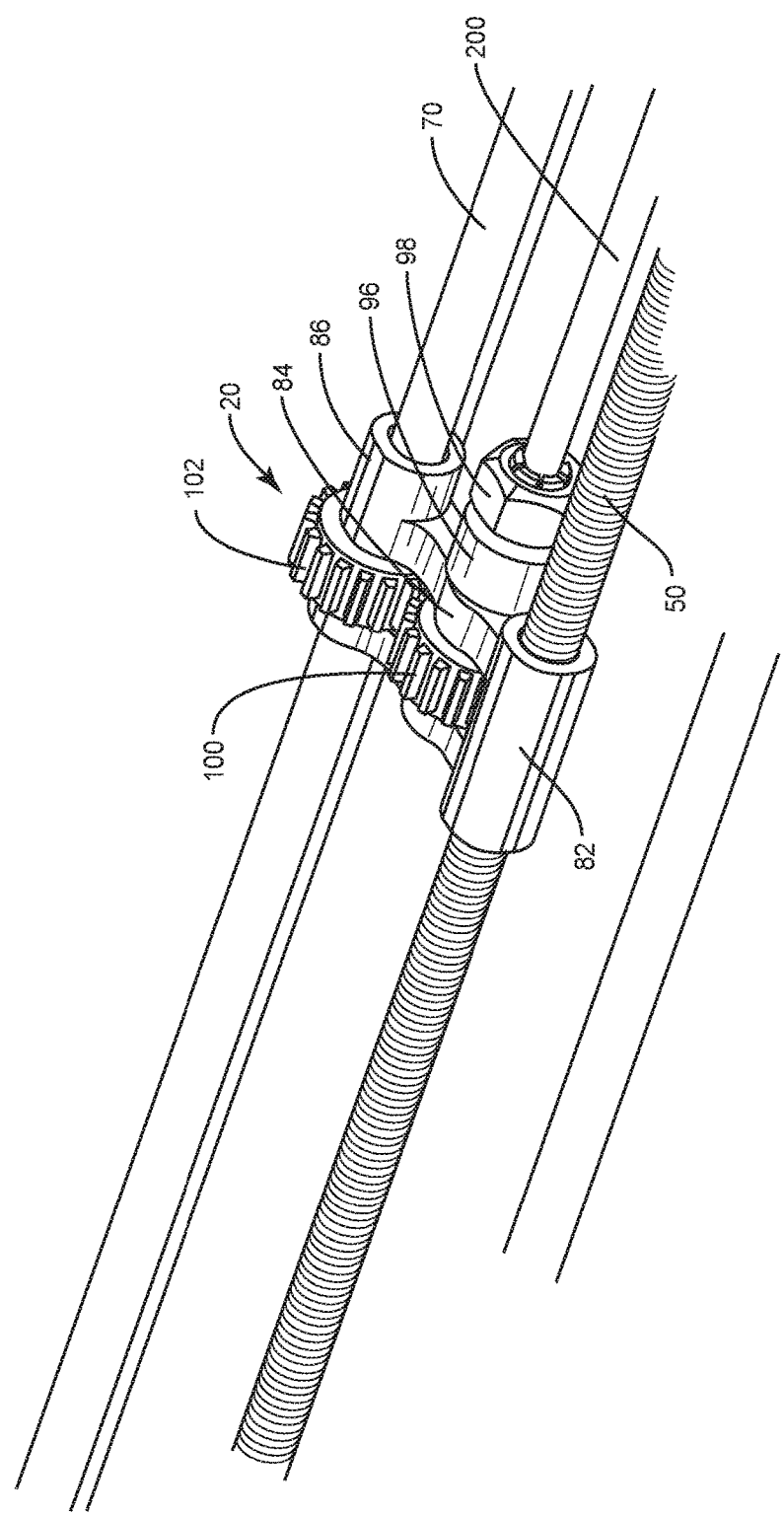
FIG. 12 is a break away view of components of the system shown in FIG. 1.
Figure 13:
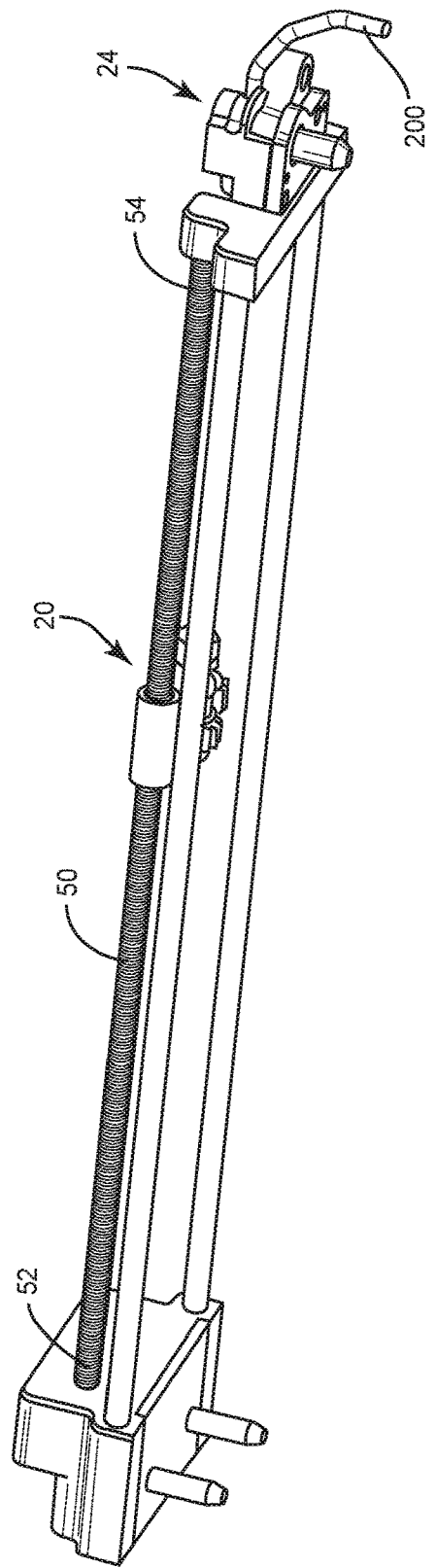
FIG. 13 is a perspective view of components of one embodiment of a spinal implant system in accordance with the principles of the present disclosure.
Figure 14:
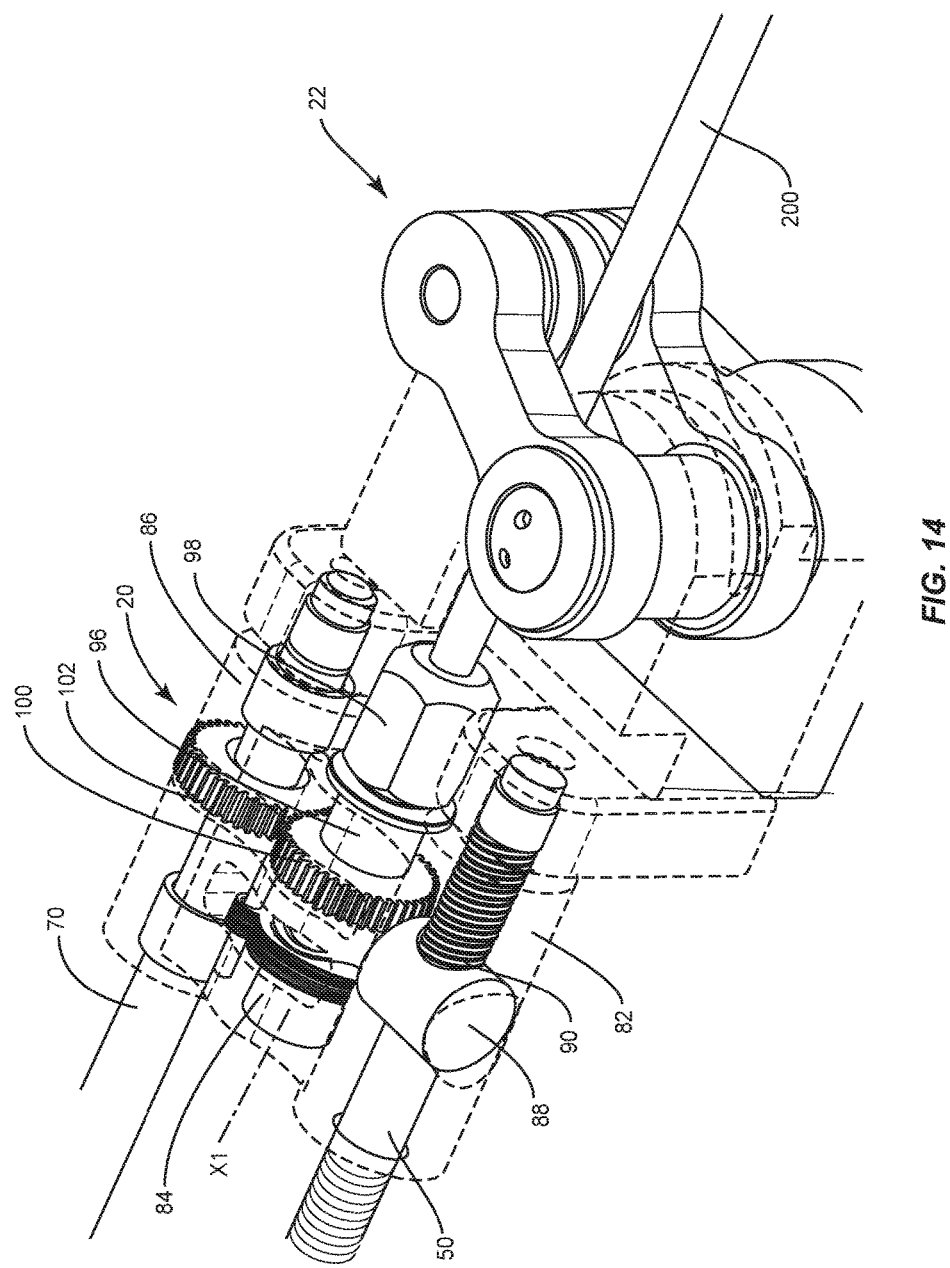
FIG. 14 is a break away view, in part phantom, of components of one embodiment of a spinal implant system in accordance with the principles of the present disclosure.
Figure 15:
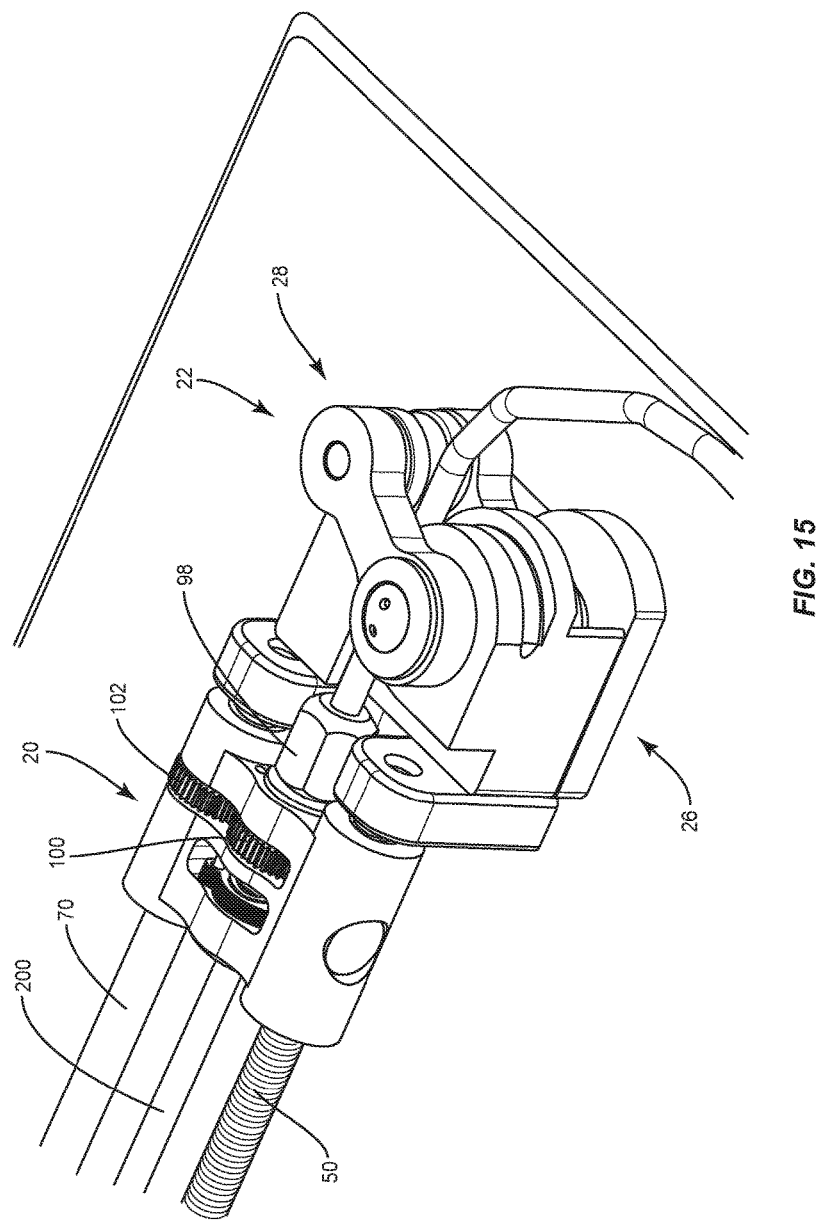
FIG. 15 is a break away view of components of one embodiment of a spinal implant system in accordance with the principles of the present disclosure.
Figure 16:
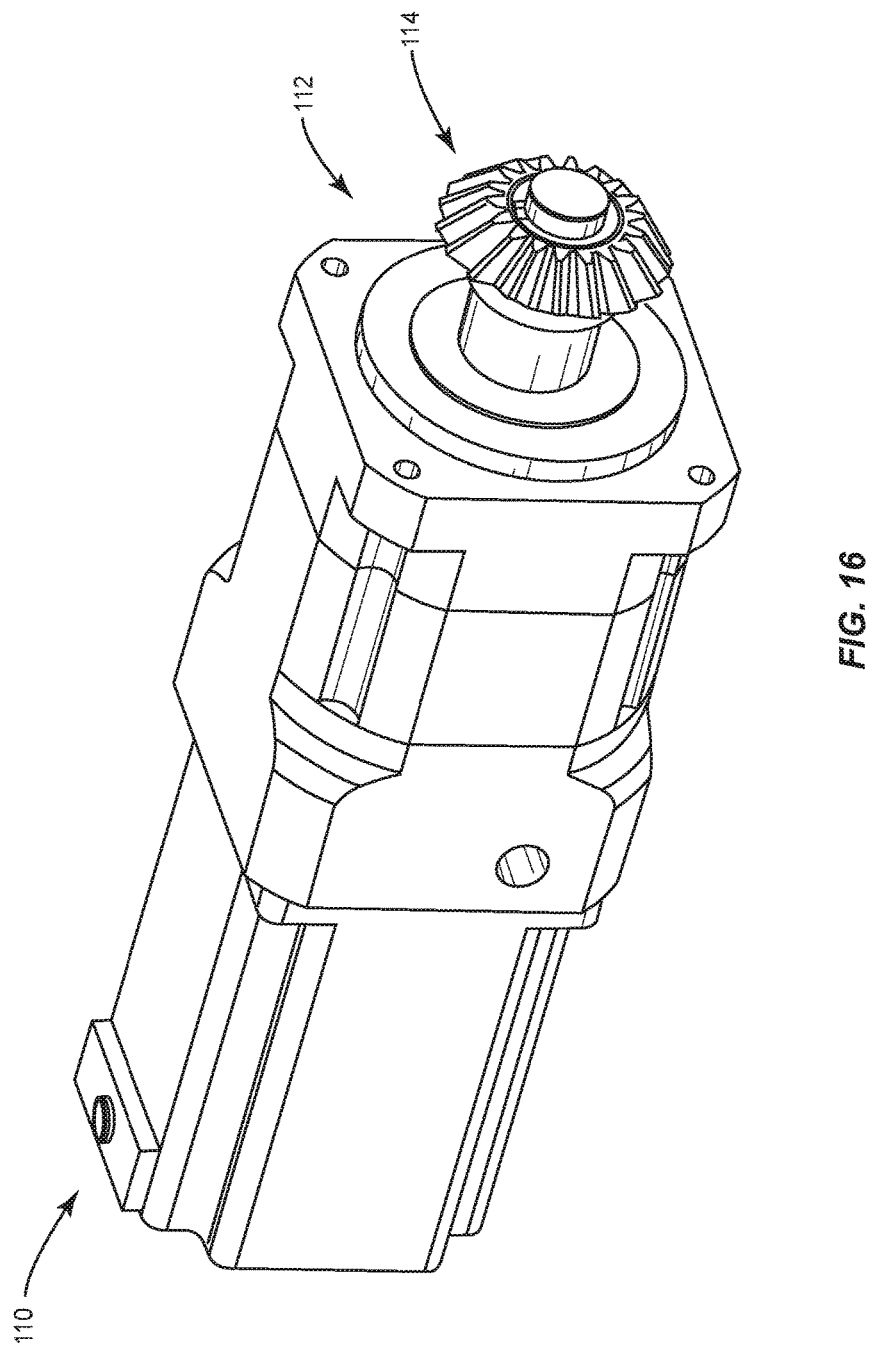
FIG. 16 is a perspective view of components of one embodiment of a spinal implant system in accordance with the principles of the present disclosure.

Displacement module 18 includes an actuator, such as, for example, a motor 42. Motor 42 is enclosed within container 40 and configured to power and rotate gear mechanisms 44, 60, as shown in FIG. 10 and described herein. In some embodiments, a portion of gear mechanisms 44, 60 are maintained within a sterile environment within container 40. Gear mechanism 44 includes meshing gears 46, 48 configured to transmit rotational motion into linear motion to translate carrier 20, as described herein. Gear 48 is connected with a drive post, such as, for example, a shaft 50. Shaft 50 extends between an end 52 and an end 54 and includes a threaded surface 56 extending therebetween. Shaft 50 is configured for disposal with carrier 20 such that shaft 50 drives and/or translates carrier 20 and spinal rod 200 along a length of shaft 50. Shaft 50 is configured to translate carrier 20 to facilitate translation of spinal rod 200 relative to mandrel 26 and arm 28 for contouring, as described herein.

Motor 42 is configured to power rotation of gear mechanism 60. Gear mechanism 60 includes meshing gears 62, 64 configured to transmit rotational motion to carrier 20 to rotate spinal rod 200 according to signals provided by computer 14, as described herein. Gear 64 is connected with a drive post, such as, for example, a shaft 70. Shaft 70 extends between an end 72 and an end 74 and includes a smooth surface 56 extending therebetween. Carrier 20 is configured for movement along shaft 70. Shaft 70 is configured to actuate rotation of spinal rod 200 in response to coordinates of a selected implant configuration provided by computer 14. For example, as spinal rod 200 translates in response to coordinates of the selected implant configuration provided by computer 14, computer 14 sends a signal to rotate spinal rod 200 to a selected angle to contour spinal rod 200 to a selected shape. Shaft 70 rotates causing carrier 20 to rotate spinal rod 200, as described herein.

In some embodiments, bending module 22 is utilized intra-operatively in a sterile environment. In some embodiments, container 40 is covered by a sterile drape 500. In some embodiments, gear mechanisms 44, 60 are enclosed by a cover 76 disposed outside of container 40. In some embodiments, cover 76 perforates drape 500 to facilitate access to carrier 20 for disposal of spinal rod 200 and movement of carrier 20 and shafts 50, 70, as described herein.

Displacement module 18 is configured as a linear slide and includes carrier 20. Carrier 20 includes a housing 80 having a portion 82, a portion 84 and a portion 86. Portion 82 includes a collar 88 having a surface 90. Surface 90 includes a threaded surface configured for a threaded engagement with shaft 50. Engagement of surface 82 with surface 56 causes carrier 20 to axially translate along shaft 50 between ends 52, 54 to effect translation of spinal rod 200 relative to implant bending device 24 to actuate contouring spinal rod 200.

Portion 84 includes a shaft 96. Shaft 96 extends along an axis X1 that defines an axis of translation and/or rotation of spinal rod 200. Shaft 96 includes an engagement part 98. Part 98 is configured for connection with spinal rod 200. In some embodiments, part 98 is configured to grip and/or clamp spinal rod 200 during translation and/or rotation relative to bending module 22, as described herein. In some embodiments, part 98 includes a chuck having an inner surface, such as, for example, a socket (not shown). The socket defines a cavity configured to mate with a portion of spinal rod 200. In some embodiments, the socket may include a shape, such as, for example, oval, oblong, triangular, square, polygonal, irregular, uniform, non-uniform, arcuate, variable and/or tapered. In some embodiments, the socket may have alternate surface configurations to enhance fixation with spinal rod 200 such as, for example, rough, arcuate, undulating, mesh, porous, semi-porous, dimpled and/or textured.

Shaft 96 is connected with a gear 100. Gear 100 is engageable with a gear 102 disposed with portion 86 and shaft 70. Gears 100, 102 actuate rotation of carrier 20 and spinal rod 200 in response to a signal from computer 14, as described herein. Portion 86 includes gear 102. Gear 102 is rotatable by shaft 70 in response to the signals from computer 14 for contouring spinal rod 200 to the selected implant configuration. Gear 102 is rotated into engagement with gear 100. Engagement of gears 100, 102 causes carrier 20 and spinal rod 200 to rotate relative to bending module 22. In some embodiments, carrier 20 applies an axial force capacity in a range of up to 680 N to spinal rod 200.

Figure 17:
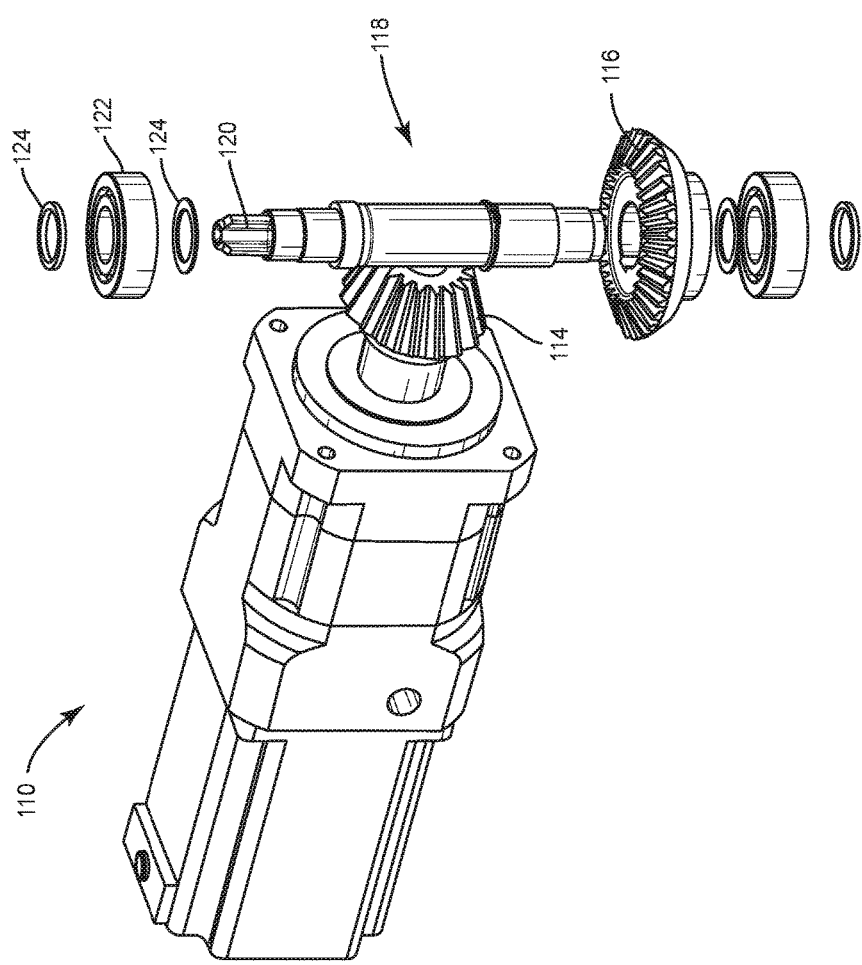
FIG. 17 is a perspective view of components of one embodiment of a spinal implant system in accordance with the principles of the present disclosure.
Figure 18:
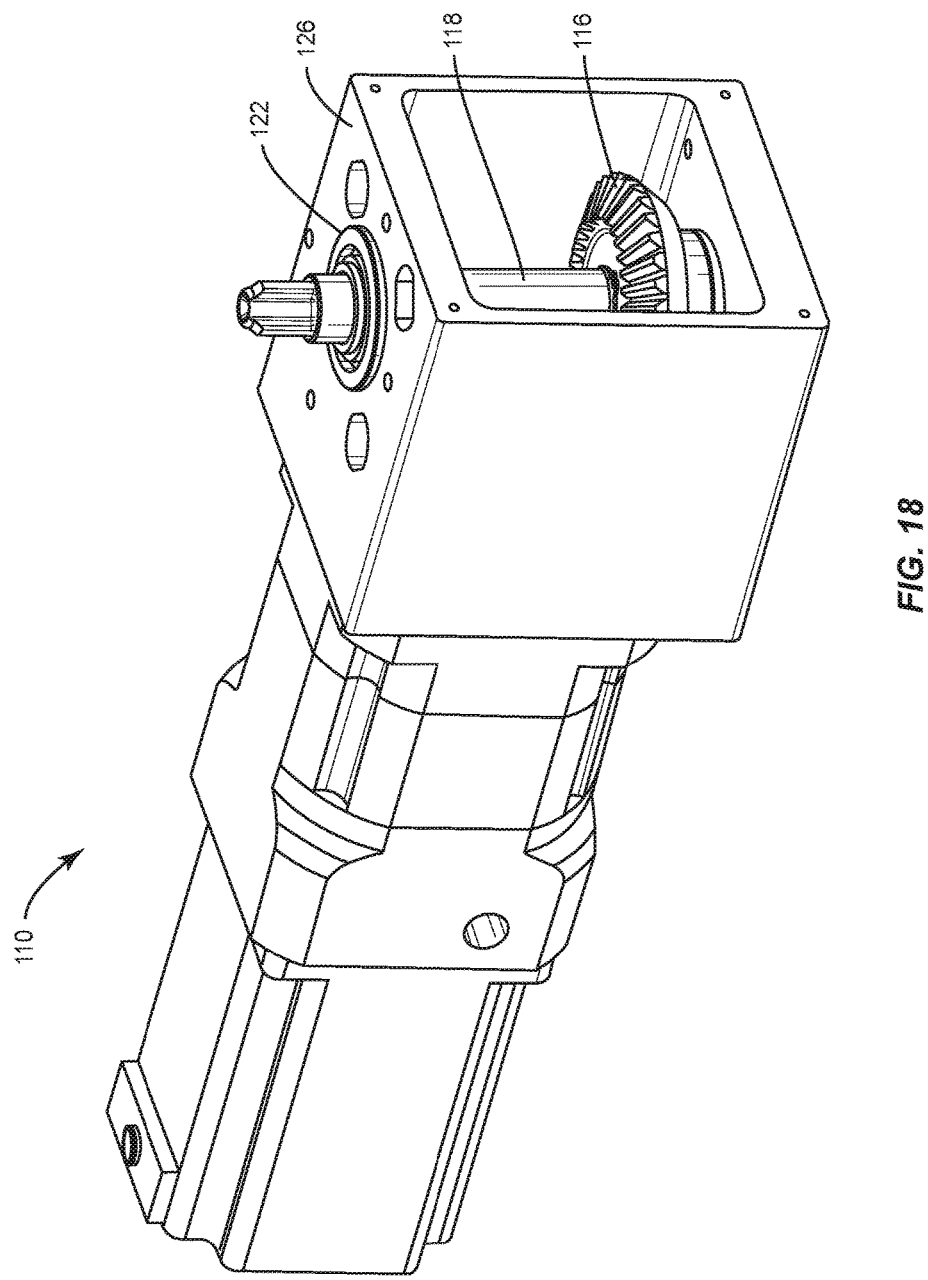
FIG. 18 is a perspective view of components of one embodiment of a spinal implant system in accordance with the principles of the present disclosure.
Figure 19:
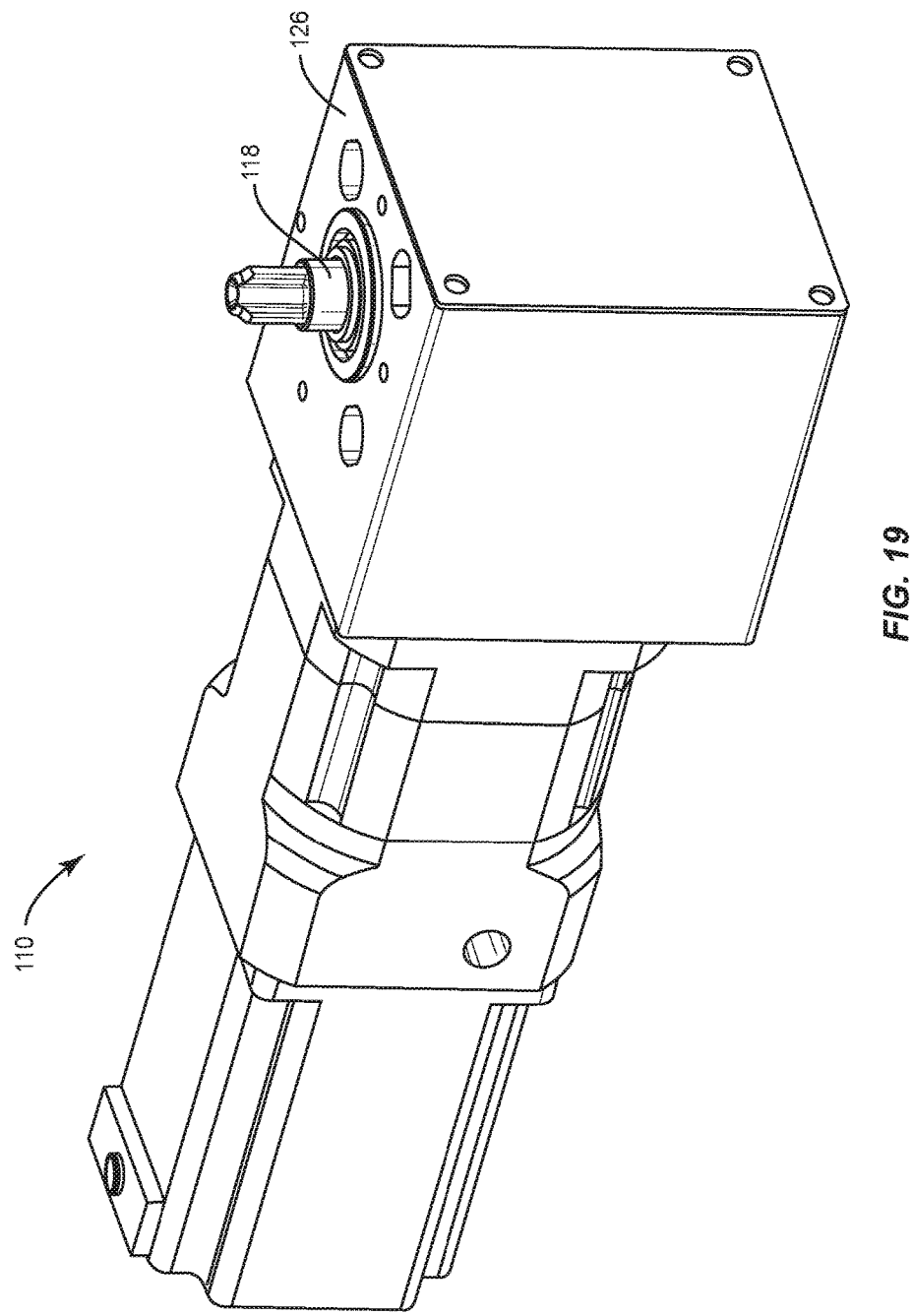
FIG. 19 is a perspective view of components of one embodiment of a spinal implant system in accordance with the principles of the present disclosure.
Figure 20:
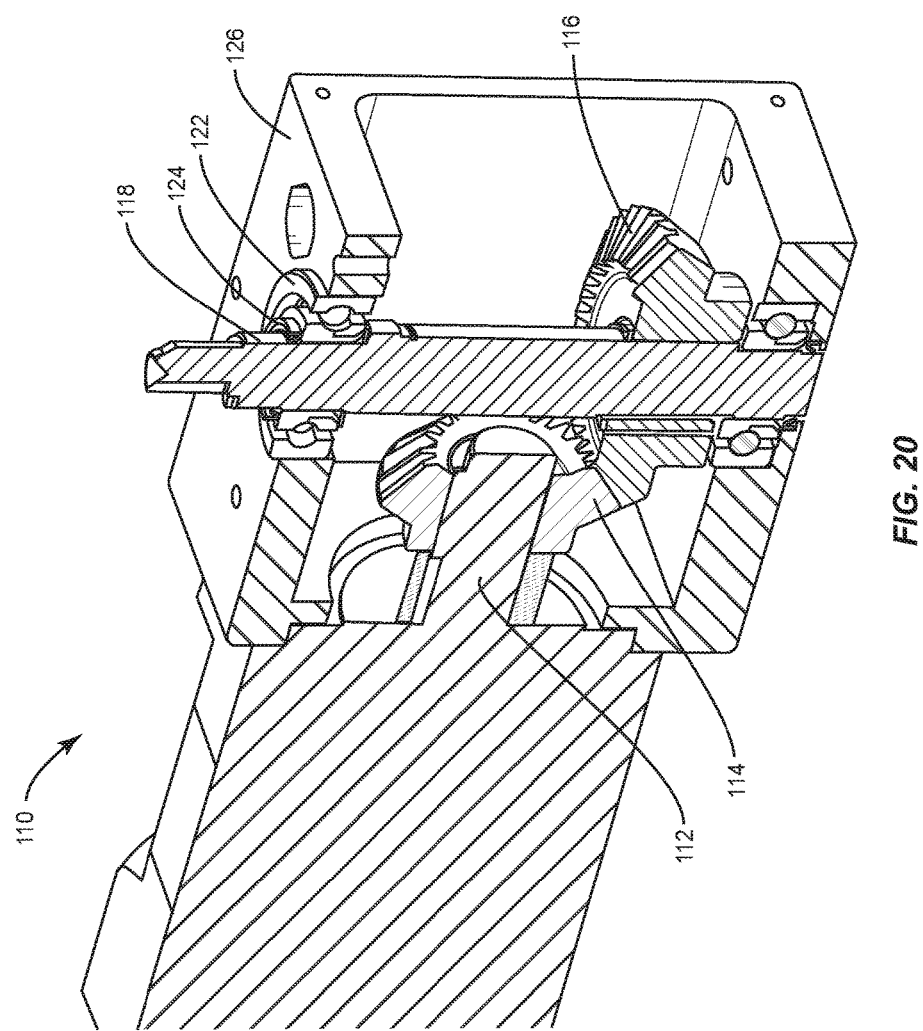
FIG. 20 is a cross section view of the components shown in FIG. 18.
Figure 21:
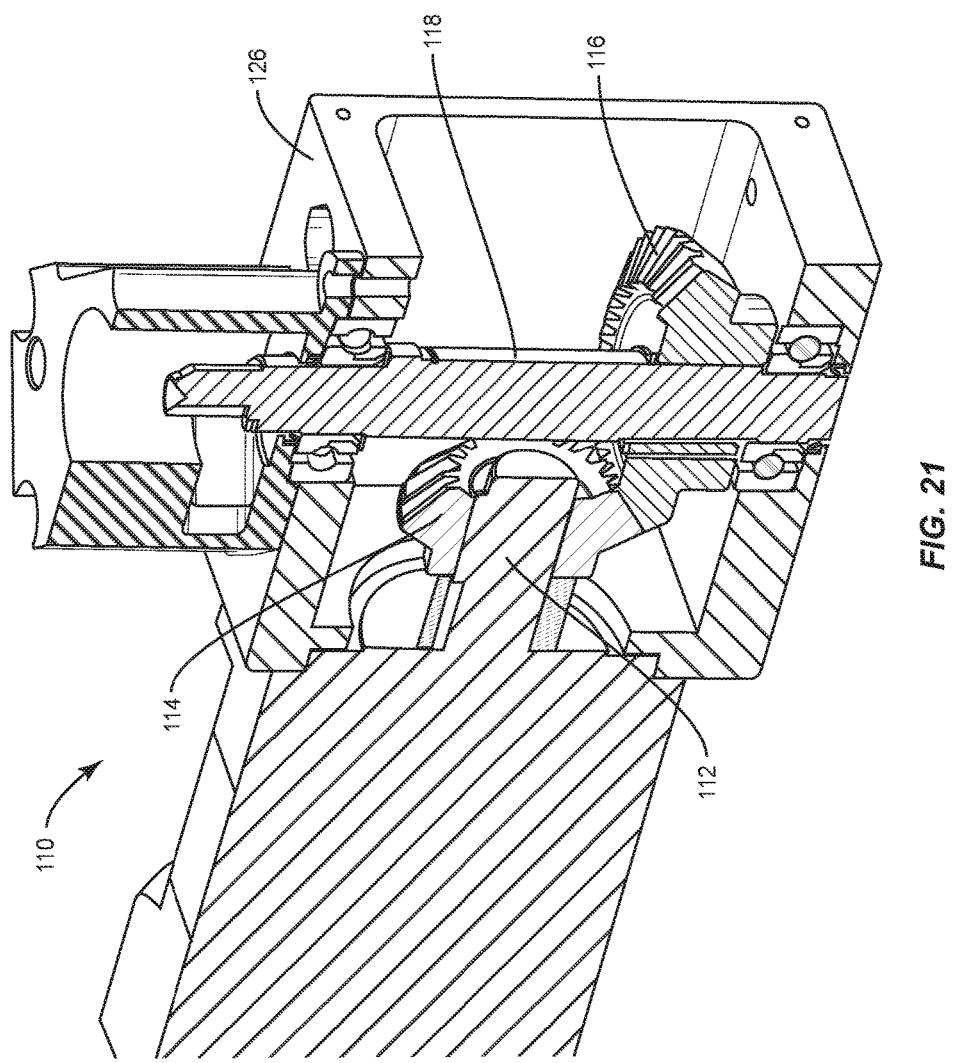
FIG. 21 is a cross section view of components of one embodiment of a spinal implant system in accordance with the principles of the present disclosure.

Bending module 22, as shown in FIGS. 14-25, includes an actuator, such as, for example, a stepper motor 110 having a drive, such as, for example, a planetary gear head 112. Gear head 112 includes a spiral bevel gear 114 engageable with a spiral bevel gear 116 of an output shaft 118, as shown in FIG. 20. In some embodiments, a gear ratio of gears 114, 116 is 10:1. In some embodiments, a maximum output torque of motor 110 is approximately 510 inch per pound force (in-lbf). Output shaft 118 includes a spline surface 120. Gears 114, 116 engage and rotate shaft 118. In some embodiments, an output of motor 110 is approximately 510 in-lbf and gears 114, 116 include a gear ratio of 3:2 such that an output torque of gears 114, 116 is approximately 765 in-lbf. In some embodiments, a maximum output torque of gears 114, 116 is approximately 900 in-lbf. In some embodiments, shaft 118 includes at least one angular contact ball bearing 122 to bear a tolerance of radial and axial loads applied to shaft 118, as shown in FIG. 17. In some embodiments, shaft 118 includes at least one grease seal 124. Shaft 118 is enclosed in a housing 126, as shown in FIG. 18.

Figure 22:
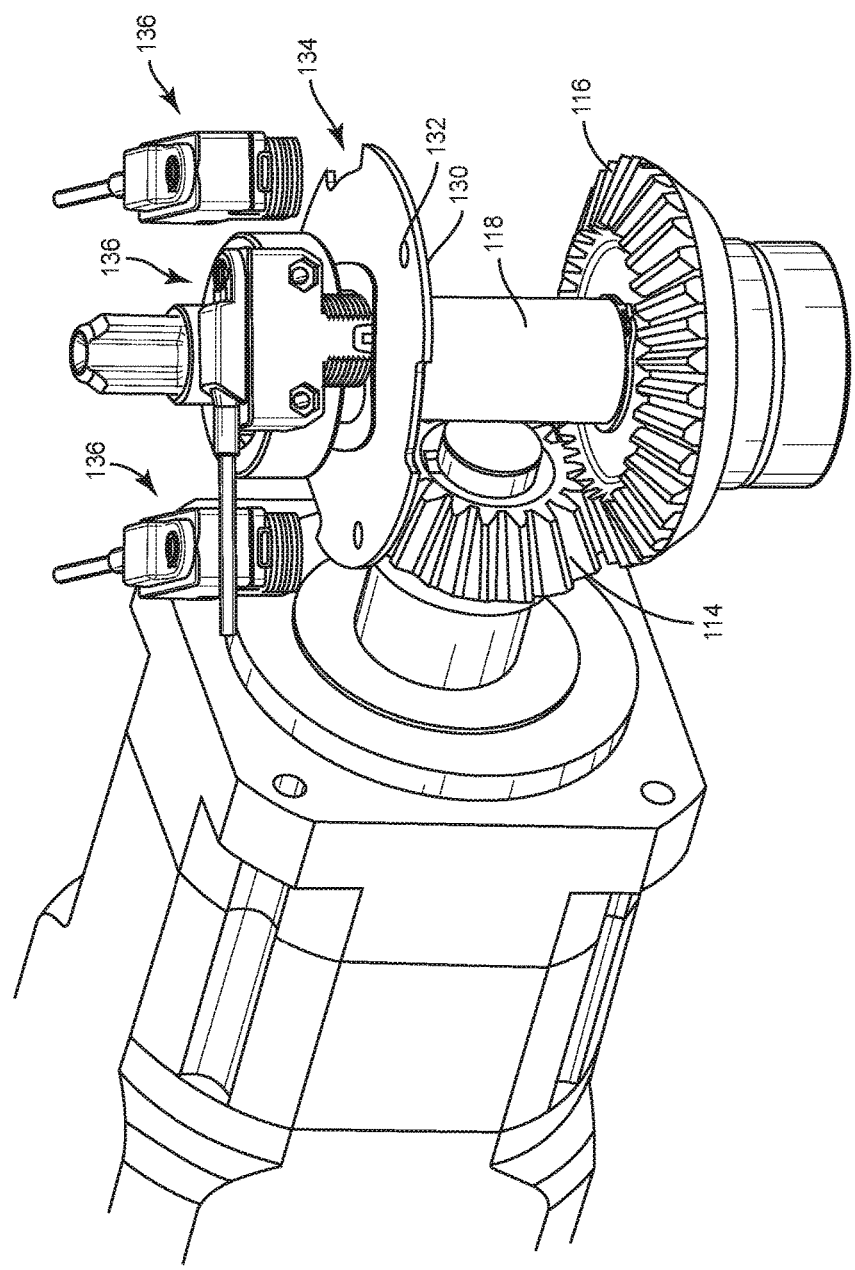
FIG. 22 is a perspective view of components of one embodiment of a spinal implant system in accordance with the principles of the present disclosure.

Bending module 22 includes a timing plate 130, as shown in FIG. 22. In some embodiments, plate 130 includes a surface that defines a plurality of openings 132 circumferentially disposed about plate 130. Openings 132 are configured to indicate an inner track, such as, for example, a home position. In some embodiments, plate 130 includes a surface that defines a plurality of notches 134. Notches 134 are configured to indicate an outer track, such as, for example, a minimum and/or maximum position. Plate 130 is configured to facilitate control and/or timing of the rotation of arm 28 in response to the signals from computer 14.

Figure 23:
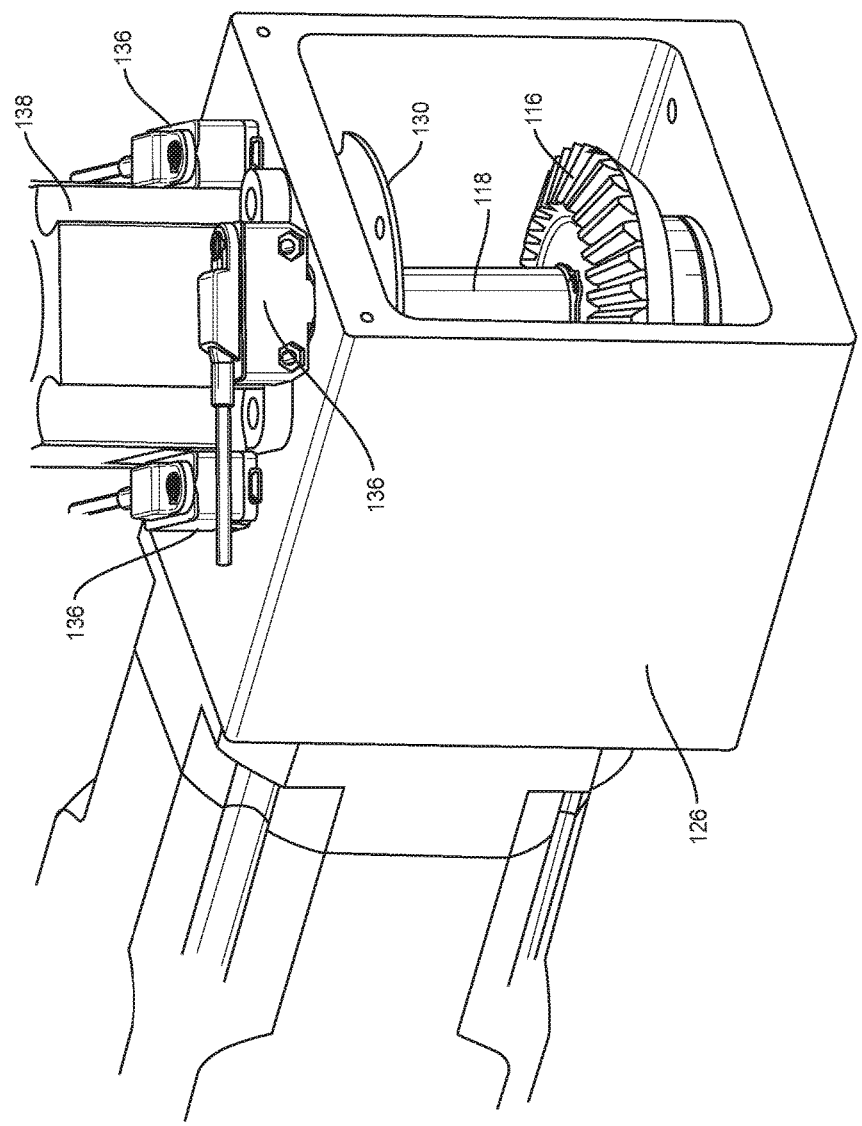
FIG. 23 is a perspective view of components of one embodiment of a spinal implant system in accordance with the principles of the present disclosure.
Figure 24:
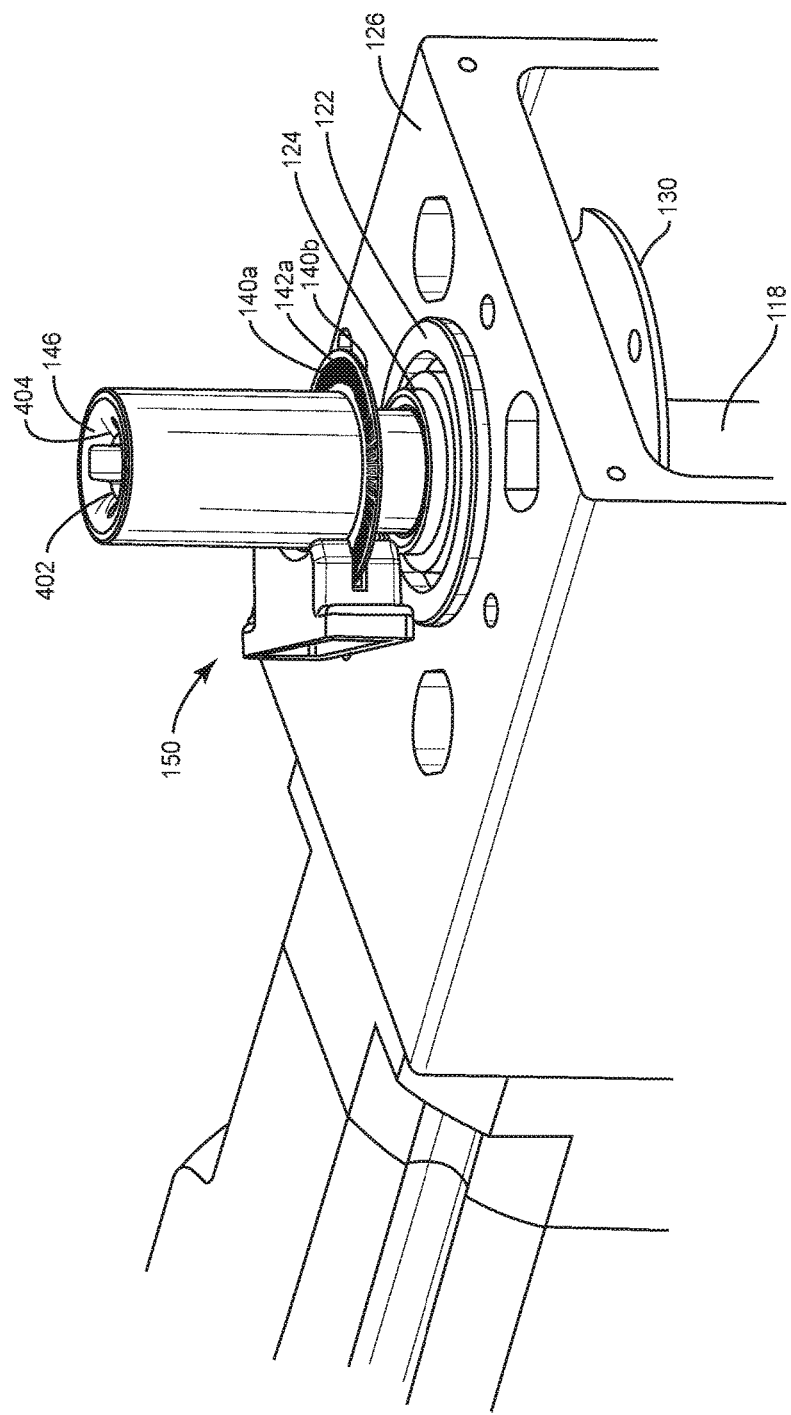
FIG. 24 is a perspective view of components of one embodiment of a spinal implant system in accordance with the principles of the present disclosure.
Figure 25:
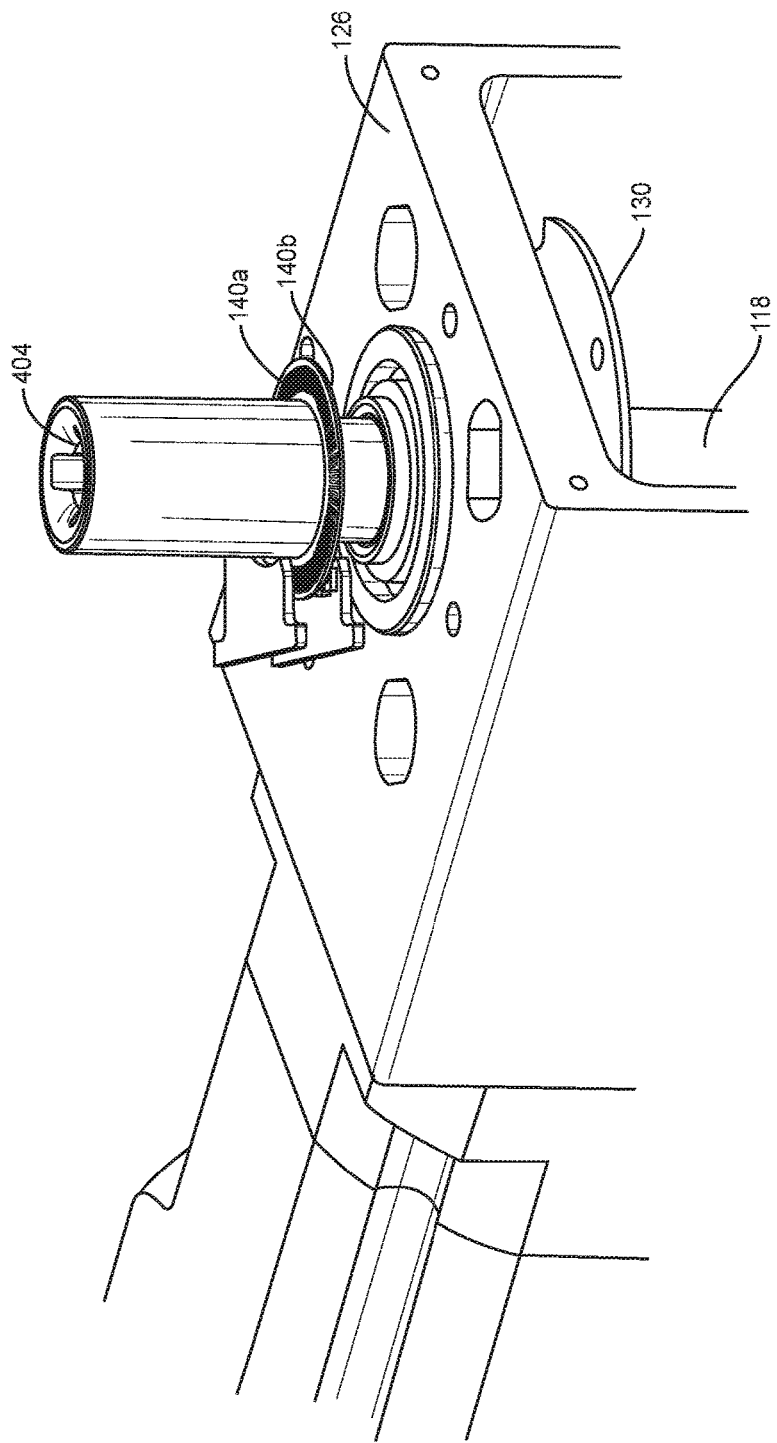
FIG. 25 is a perspective view of the components shown in FIG. 24.
Figure 26:
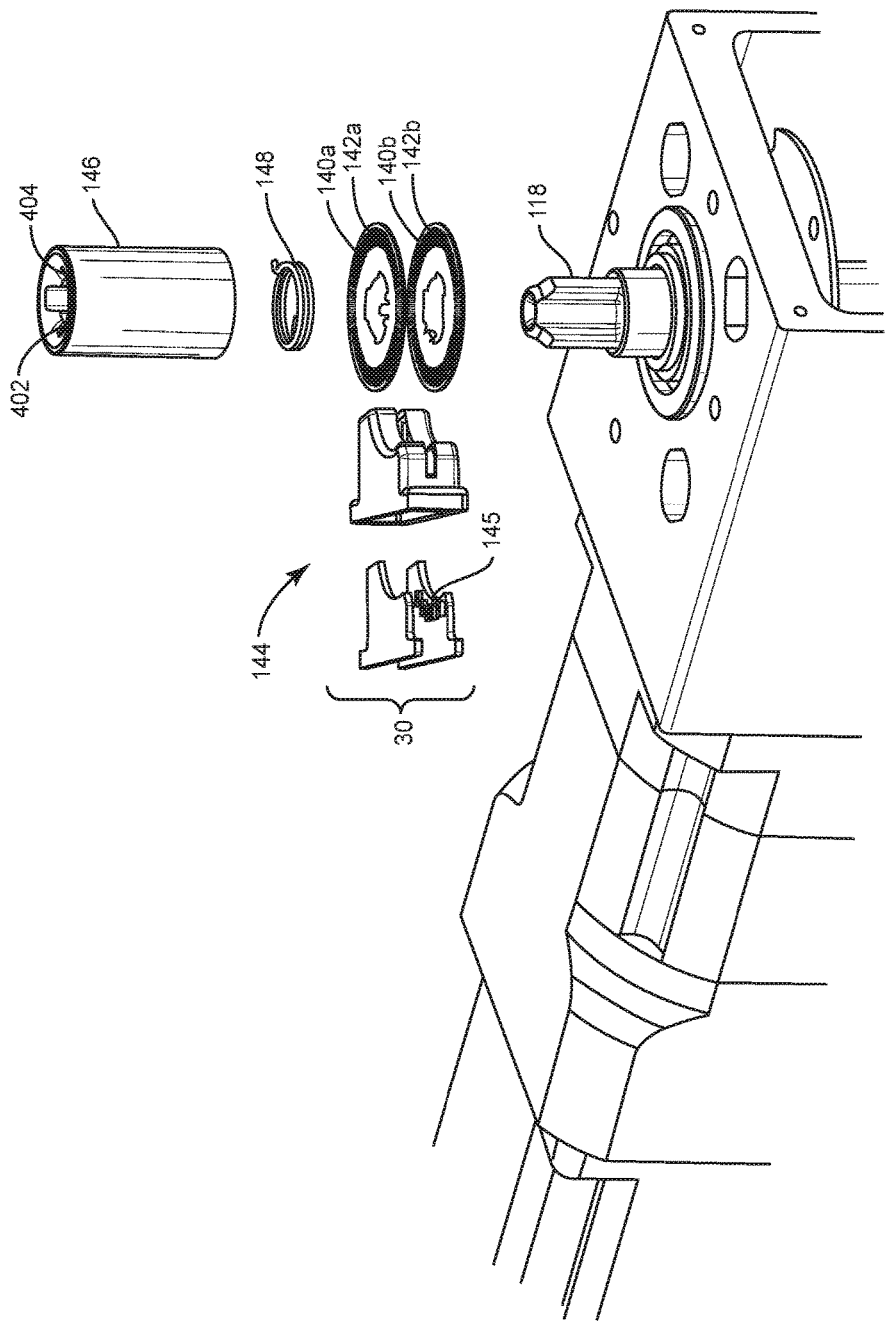
FIG. 26 is a perspective view of the components shown in FIG. 25 with parts separated.
Figure 27:
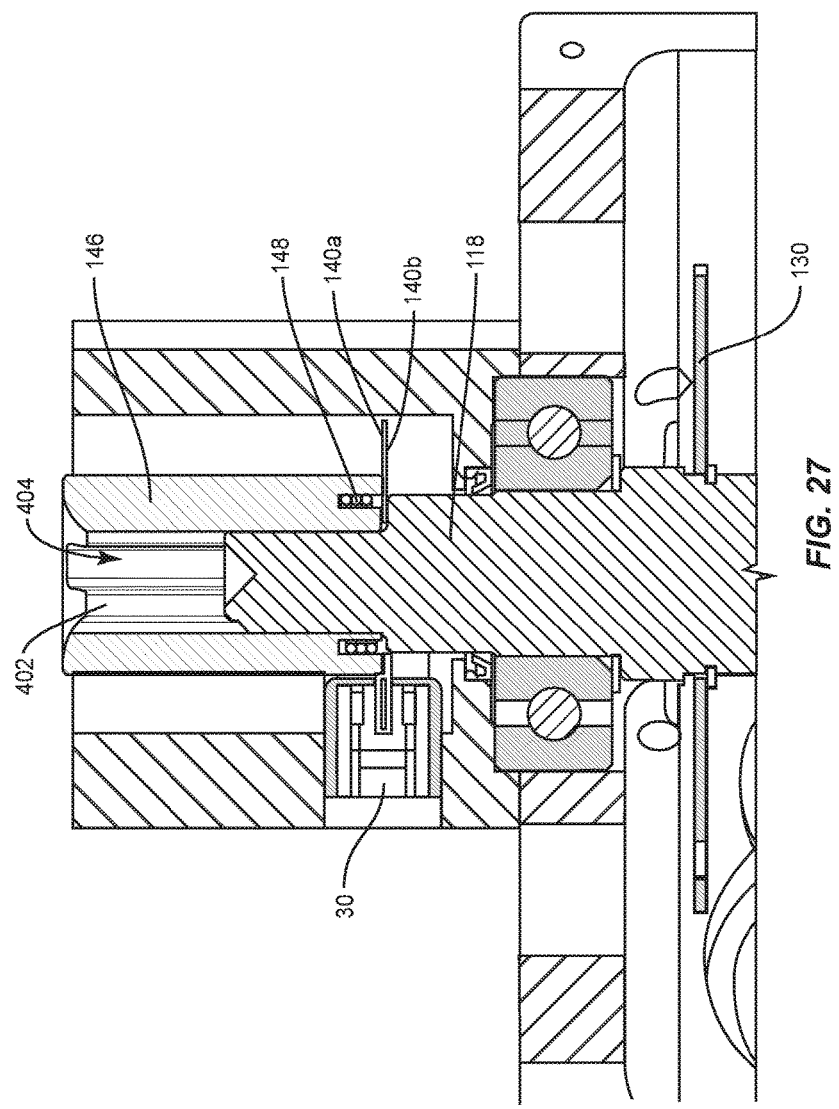
FIG. 27 is a cross section view of the components shown in FIG. 23.

In some embodiments, plate 130 operates in conjunction with sensors, such as, for example, optical sensors 136 disposed about plate 130, as shown in FIG. 22. Sensors 136 are disposed adjacent to a housing 138, as shown in FIG. 23. Sensors 136 are configured to sense a reflection of light emitted from plate 130 to track and/or gauge rotation of arm 28. Sensors 136 comprise electronic detectors that convert light, or a change in light, into an electronic signal to indicate movement of arm 28.

Contact sensor 30, as shown in FIGS. 24-29, detects contact/non-contact of arm 28 with spinal rod 200 and facilitates applying a selected bend to spinal rod 200. Contact sensor 30 is configured to sense a spring-back of spinal rod 200 after spinal rod 200 is contoured. The spring back of spinal rod 200 facilitates detection if the proper bend was effected by arm 28. In some embodiments, contact sensor 30 includes an electromechanical mechanism that can determine when arm 28 of implant bending device 24 makes initial contact with spinal rod 200, or breaks contact with spinal rod 200 after a bend to determine the resulting bend angle.

Contact sensor 30 includes one or more elements, such as, for example, optical discs 140a, 140b. Discs 140a, 140b include indicia, such as, for example, such as, for example, openings 142a, 142b. In some embodiments, the indicia of discs 140a, 140b can include etched surfaces, interference patterns and/or openings having various geometric configurations, similar to those described herein.

A coupler 146 is connected with shaft 118 and transmits rotational movement to arm 28 from shaft 118 for bending spinal rod 200. Disc 140a is mounted with coupler 146 and connected with a torsion spring 148 disposed with coupler 146. Disc 140b is mounted with shaft 118. Torsion spring 148 is connected with coupler 146 to bias disc 140a relative to disc 140b such that openings 142a, 142b are disposed in an aligned orientation, as described herein. In some embodiments, the connection of torsion spring 148 with discs 140a, 140b comprises a clutch.

Contact sensor 30 includes an emitter/detector 144 having a printed circuit board (PCB) 145. In some embodiments, PCB 145 mechanically supports and electrically connects electronic components using conductive tracks, pads and other features etched from copper sheets laminated onto a non-conductive substrate. PCB 145, in connection with the components of contact sensor 30, facilitates sensing of touch-on and touch-off positions of arm 28 relative to spinal rod 200 such that contact sensor 30 sends signals to computer 14 to indicate and record angular measurement for touch and release points, and real time angular adjustments of bending spinal rod 200, which can be displayed from a graphical interface, as described herein.

In some embodiments, contact sensor 30 provides feedback to define angular relationships of portions of a spinal rod and provides the ability to adjust a bending cycle to yield a selected bend output. In some embodiments, contact sensor 30 allows for adjustment of angular relationships in real time and/or during an intra-operative bending procedure. In some embodiments, contact sensor 30 facilitates determination of when arm 28 makes initial contact with spinal rod 200, or breaks contact with spinal rod 200 after a bend. In some embodiments, contact sensor 30 provides data and/or indicia of non-contact with spinal rod 200 and engagement with spinal rod 200.

In some embodiments, contact sensor 30 allows implant bending device 24 to define angular measurements based on contact sensor 30 reading touch-on and touch-off positions of arm 28 relative to spinal rod 200. In some embodiments, contact sensor 30 senses angular measurement and adjusts to a defined angle, in real time and/or intra-operatively, and can address spring back, rod diameter and rod inconsistencies. In some embodiments, contact sensor 30 provides detection sensing capability, which could be utilized to bend scoliosis configurations intra-operatively.

Figure 28:
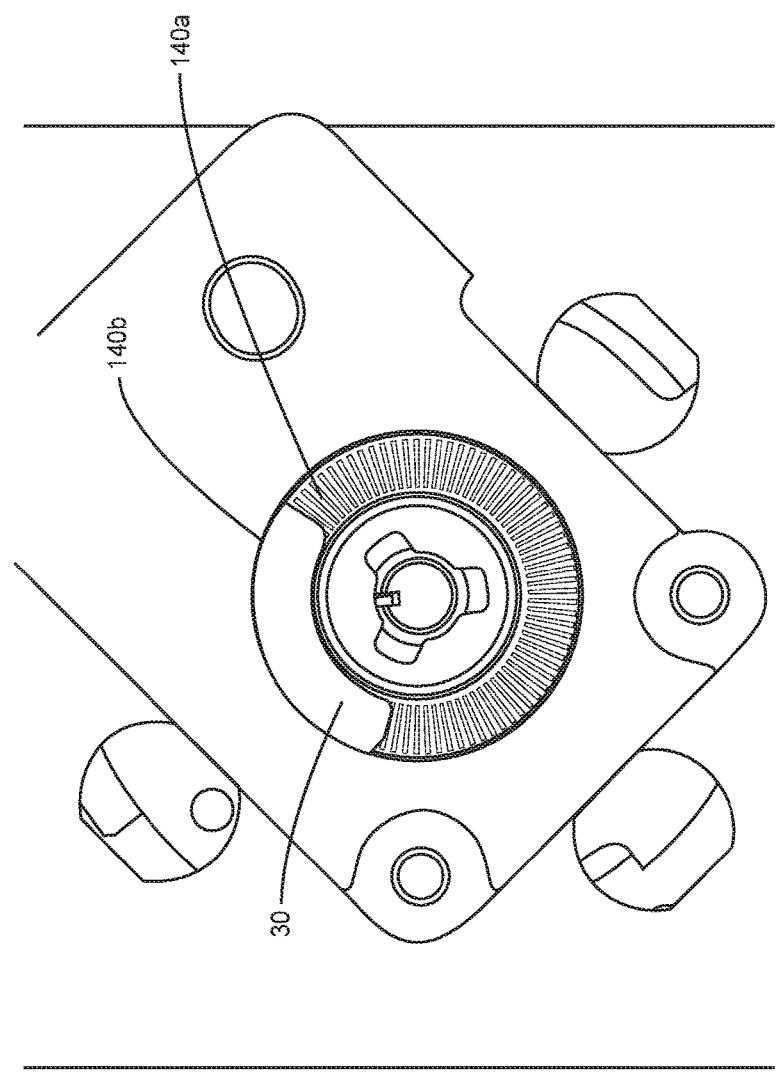
FIG. 28 is a top view of the components shown in FIG. 23.

For example, as arm 28 approaches spinal rod 200, torsion spring 148 biases disc 140a relative to disc 140b such that openings 142a, 142b are disposed in an aligned orientation and an open configuration, as shown in FIG. 28. Openings 142a, 142b are aligned for passage of a medium, such as, for example, light that is detectable by emitter/detector 144, and arm 28 and spinal rod 200 are in a non-contacting relation. In the non-contacting orientation of arm 28 and spinal rod 200, contact sensor 30 detects light emitted through the aligned orientation of openings 142a, 142b and transmits a signal, as described herein, to computer 14 to provide data and/or indicia of non-contact of arm 28 with spinal rod 200, which can be displayed from a graphical interface, as described herein. In some embodiments, the data and/or indicia can correspond to and include touch-on and touch-off positions of arm 28 relative to spinal rod 200, and/or related angular adjustment.

Figure 29:
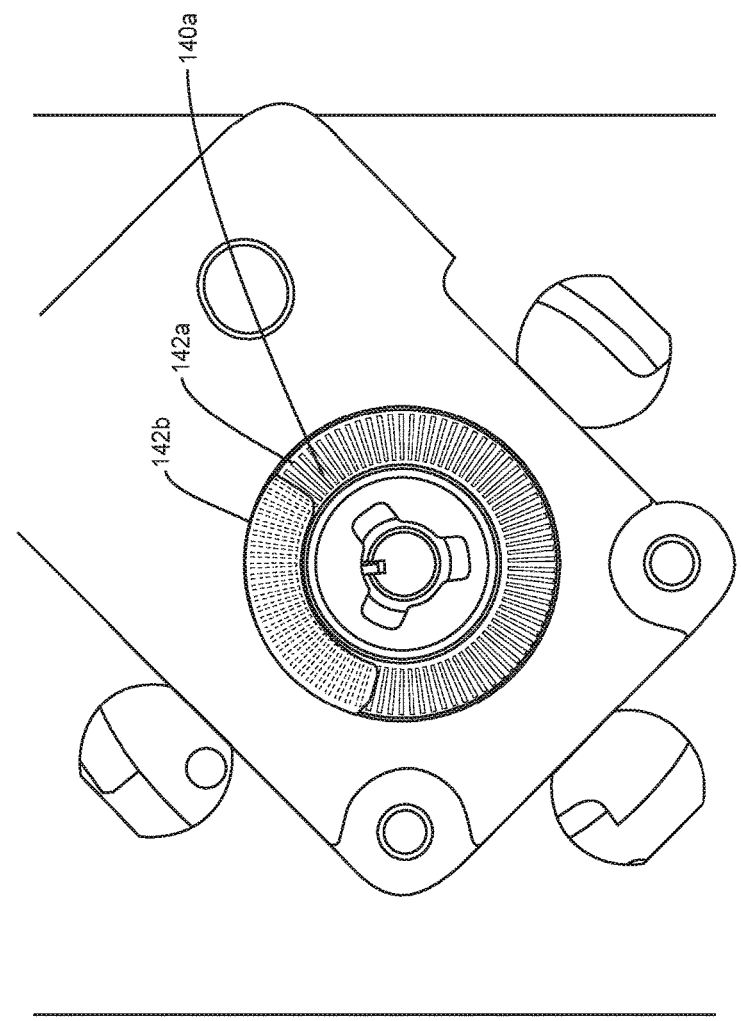
FIG. 29 is a top view of the components shown in FIG. 23.

As arm 28 contacts spinal rod 200, the initial contact bending force of arm 28 with spinal rod 200 activates the components of contact sensor 30. As arm 28 engages spinal rod 200, coupler 146 encounters a resistance that overcomes the bias of torsion spring 148 and causes disc 140a to rotate relative to disc 140b for a limited and/or selected incremental degree of relative rotation. The relative rotation of discs 140a, 140b creates a difference in openings 142a, 142b such that discs 140a, 140b are oriented out of alignment and disposed in a closed configuration, as shown in FIG. 29. The non-aligned pattern of discs 140a, 140b is sensed and/or viewed by emitter/detector 144. In some embodiments, contact sensor 30 is activated by a change in the pattern of disc 140a, 140b when bending starts and when bending ends.

Discs 140a, 140b are disposed in a non-aligned orientation when arm 28 and spinal rod 200 are in an engaging relation. In the engaging orientation of arm 28 and spinal rod 200, openings 142a, 142b are not aligned and block transmission of light such that contact sensor 30 cannot detect the emitted light and transmits a signal, as described herein, to computer 14 to provide data and/or indicia of engagement of the arm 28 with spinal rod 200, which can be displayed from a graphical interface, as described herein.

Figure 30:
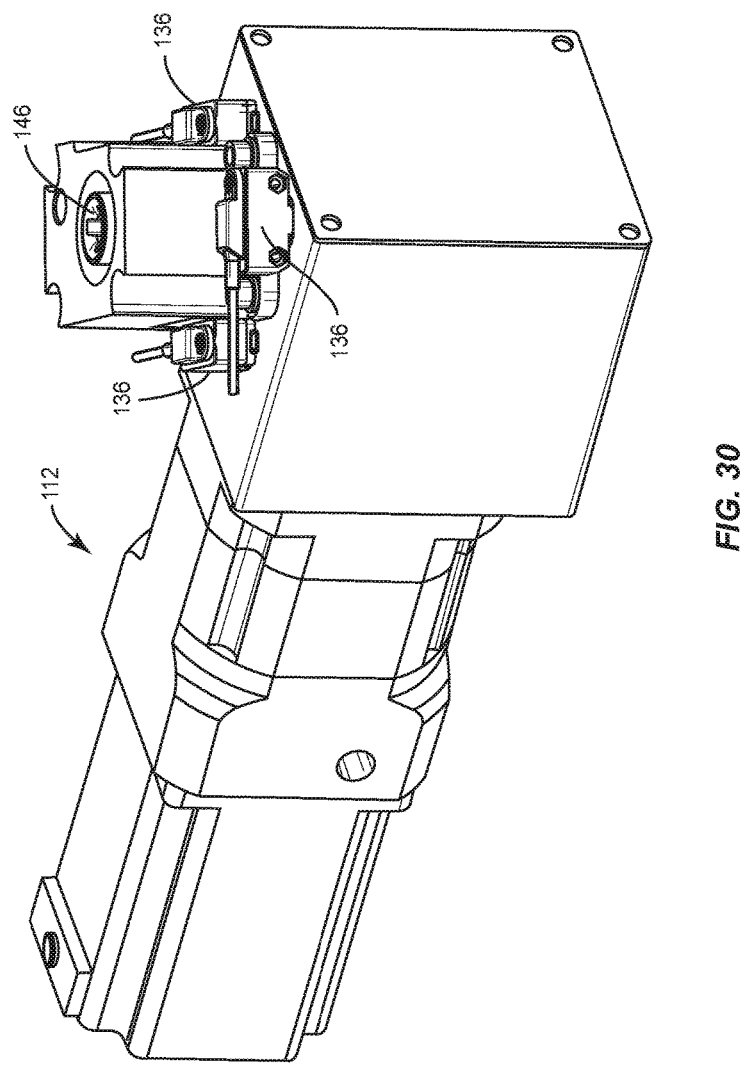
FIG. 30 is a perspective view of components of one embodiment of a spinal implant system in accordance with the principles of the present disclosure.
Figure 31:
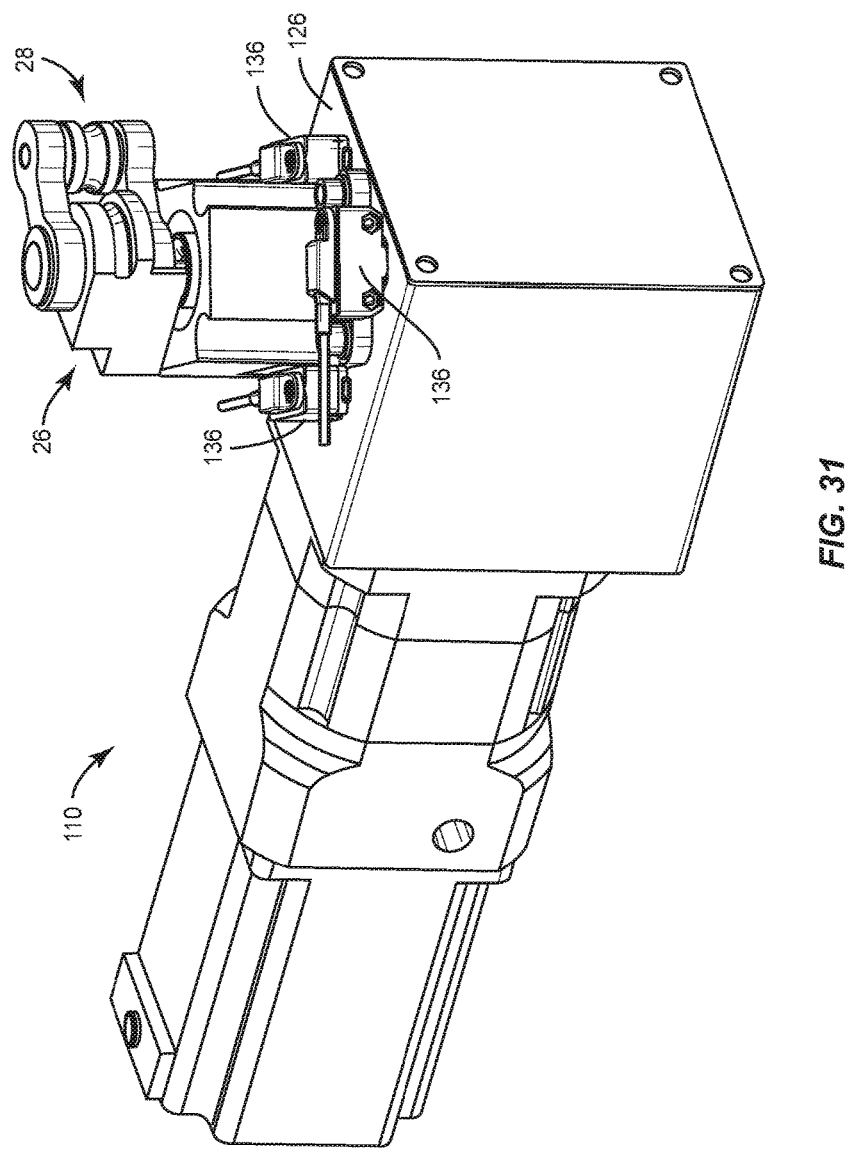
FIG. 31 is a perspective view of components of one embodiment of a spinal implant system in accordance with the principles of the present disclosure.
Figure 32:
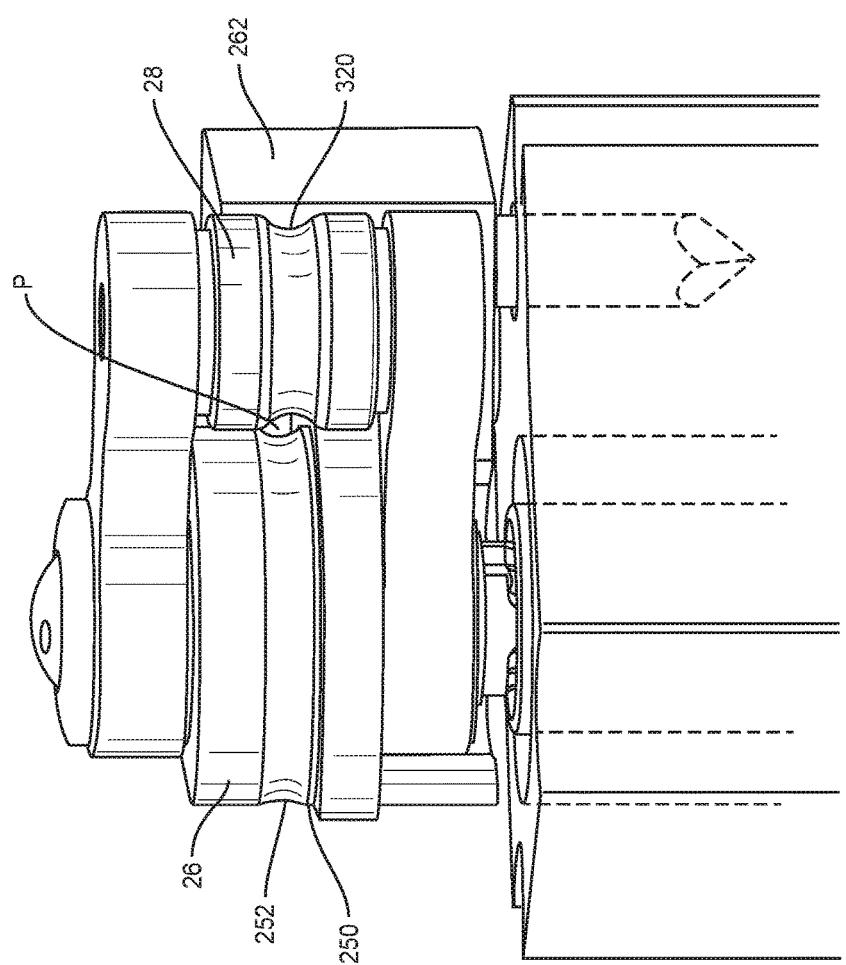
FIG. 32 is a break away view of components of the system shown in FIG. 31.
Figure 33:
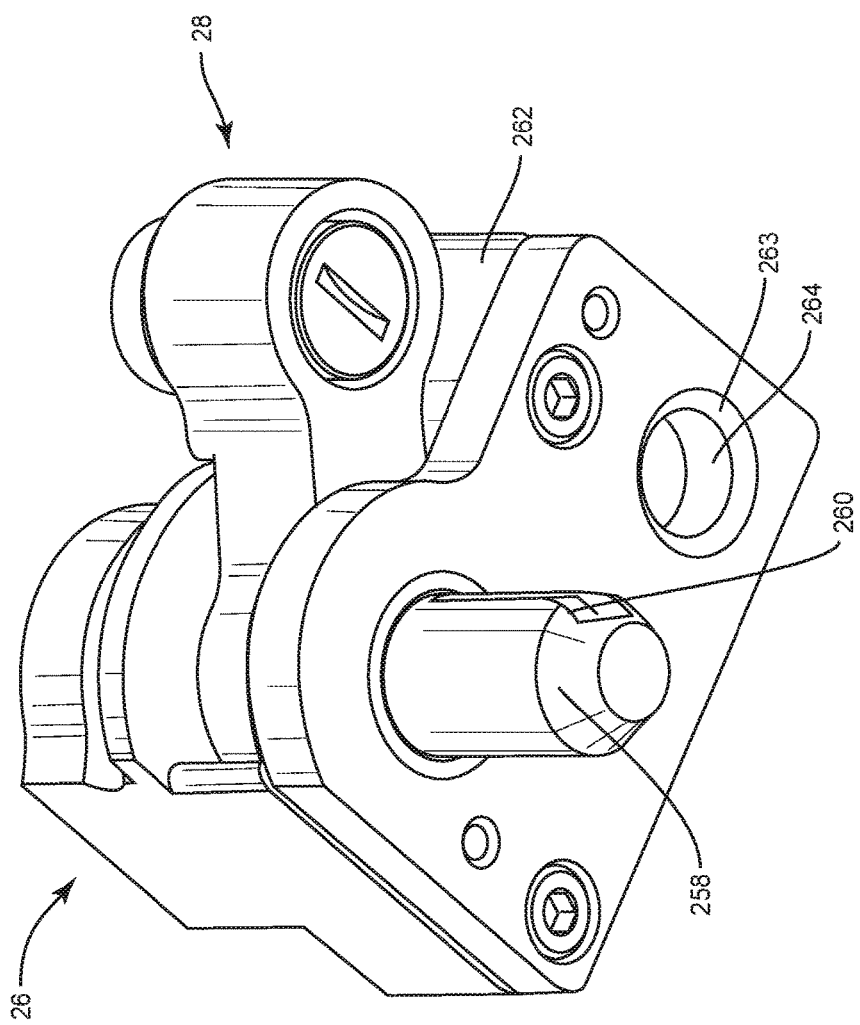
FIG. 33 is a perspective view of components of one embodiment of a spinal implant system in accordance with the principles of the present disclosure.

Mandrel 26 includes a surface 250 having a substantially curved configuration to facilitate contouring of spinal rod 200, as shown in FIGS. 30-32. Surface 250 defines a circumferential groove 252 configured to facilitate engagement with spinal rod 200. In some embodiments, surface 250 is smooth to facilitate translation and/or rotation of spinal rod 200 relative to mandrel 26. Mandrel 26 is disposed in a spaced apart relation relative to arm 28 such that mandrel 26 and arm 28 define a pathway P to facilitate passage of spinal rod 200, as shown in FIG. 32. Mandrel 26 includes a surface 254 that defines an opening 256. Opening 256 is configured for disposal of a shaft 258. Shaft 258 includes a splined end surface 260 configured for engagement with coupler 146. Engagement of surface 260 with coupler 146 is configured to facilitate selective rotation of arm 28, as described herein.

Mandrel 26 includes a wall 262. Wall 262 is configured as a stop surface to resist and/or prevent rotation of arm 28, as described herein. Wall 262 includes a surface 263 that defines an opening 264. Opening 264 is configured for disposal of an anti-rotation shaft 266.

Figure 34:
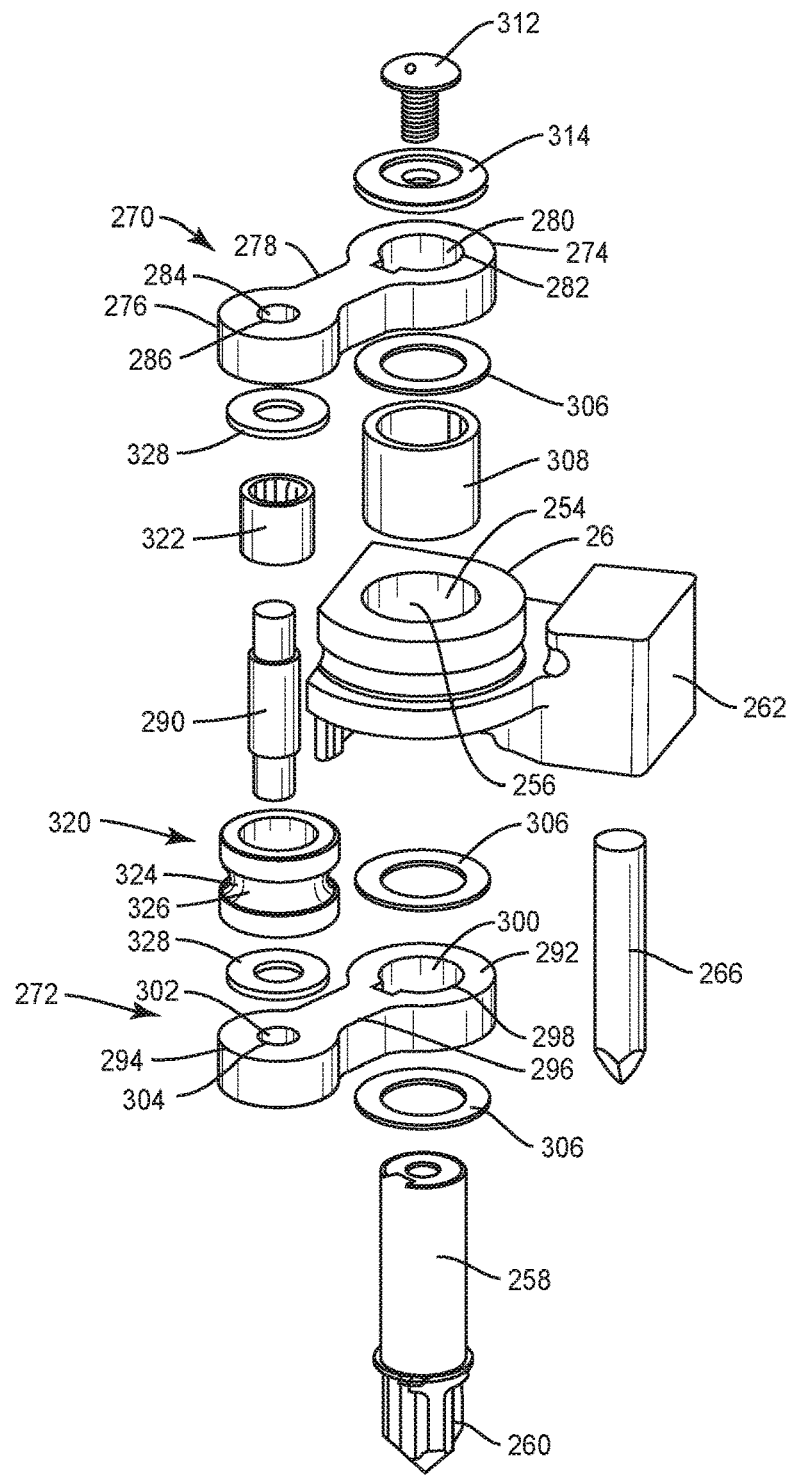
FIG. 34 is a perspective view of the components shown in FIG. 33, with parts separated.

Arm 28 includes a part 270 and a part 272. Part 270 includes a circular portion 274, a circular portion 276 and an extension 278 therebetween. Portion 274 includes a surface 280 that defines an opening 282. Opening 282 is configured for alignment with opening 256 and for disposal of a portion of shaft 258 to actuate rotation of arm 28, as described herein. Portion 276 includes a surface 284 that defines an opening 286. Opening 286 is configured for alignment with an opening of a part 272, as described herein. Opening 286 is configured for disposal of an end of a roller shaft 290, as shown in FIG. 34.

Part 272 includes a circular portion 292, a circular portion 294 and an extension 296 therebetween. Portion 292 includes a surface 298 that defines an opening 300. Opening 300 is configured for alignment with opening 256 and for disposal of a portion of shaft 258 to actuate rotation of arm 28, as described herein. Portion 294 includes a surface 302 that defines an opening 304. Opening 304 is configured for alignment with an opening of a part 270, as described herein. Opening 304 is configured for disposal of an end of a roller shaft 290.

Arm 28 is attached with mandrel 26 by aligning openings 282, 256, 300. In some embodiments, washers 306 are utilized. In some embodiments, a bushing 308 is disposed with opening 256 to facilitate rotation of arm 28. In some embodiments, bushing 308 comprises PTFE-line fiberglass. A screw 312 and cap washer 314 are disposed within openings 282, 256, 300 such that screw 312 engages a surface of shaft 258 to fix arm 28 with shaft 258 to facilitate actuation of arm 28.

Figure 35:
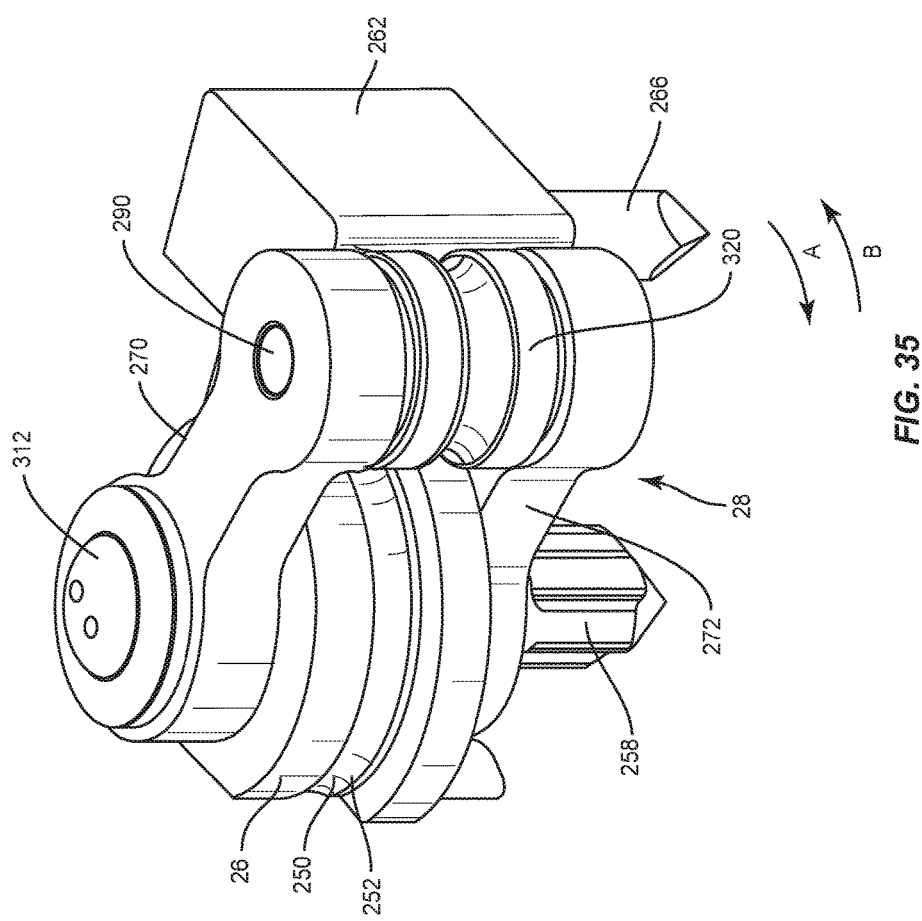
FIG. 35 is a perspective view of components of one embodiment of a spinal implant system in accordance with the principles of the present disclosure.
Figure 36:
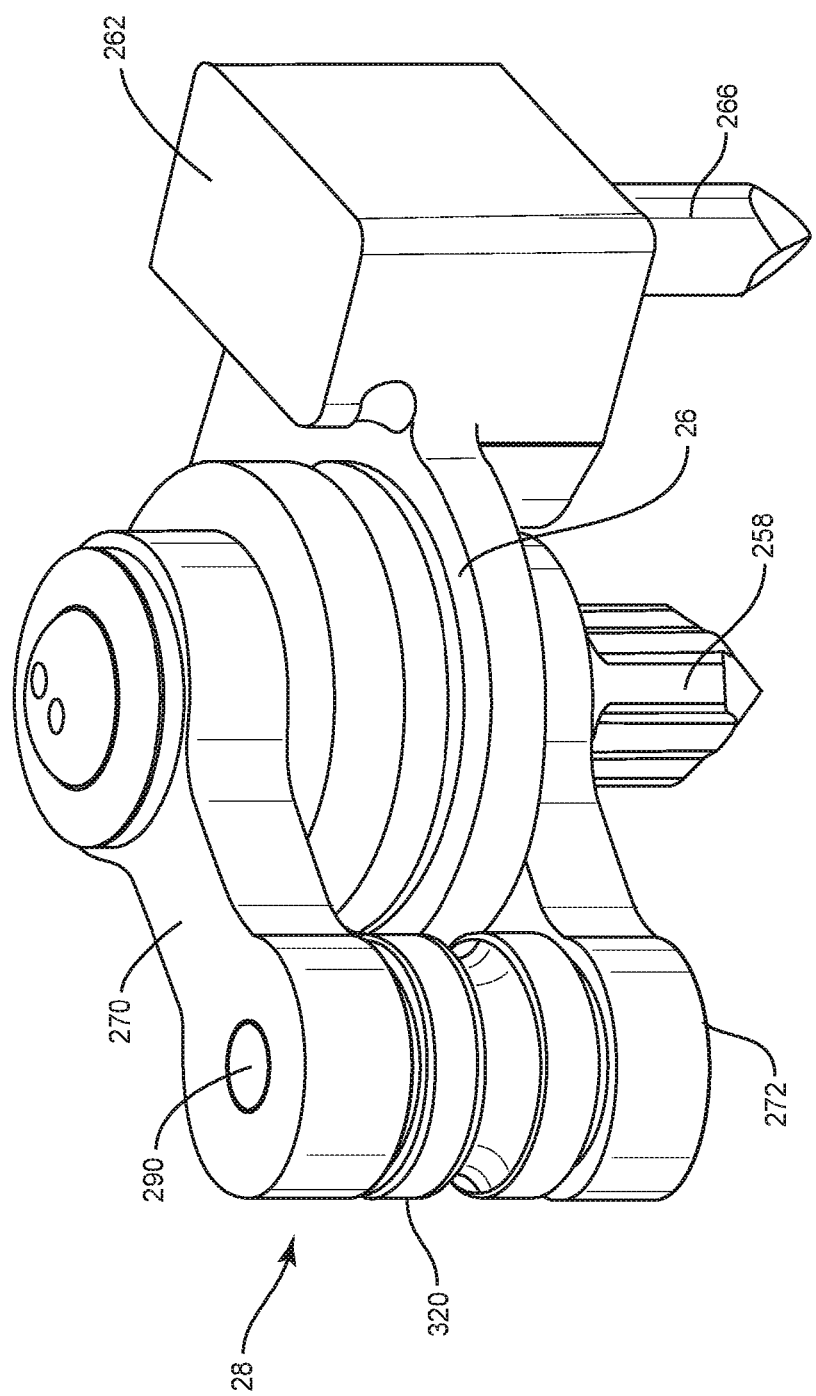
FIG. 36 is a perspective view of components of one embodiment of a spinal implant system in accordance with the principles of the present disclosure.

Openings 286, 304 are aligned along shaft 290. A roller 320 and a needle bearing 322 are disposed between portions 276, 294, as shown in FIGS. 34-36. Roller 320 includes a surface 324 having a substantially curved configuration. In some embodiments, surface 324 defines a circumferential groove 326 configured to facilitate engagement with and application of a force to spinal rod 200. In some embodiments, surface 324 is smooth to facilitate translation and/or rotation of spinal rod 200 relative to surface 324. In some embodiments, washers 328 are utilized to facilitate transmission of axial forces in the rotating components and to maintain the components aligned along shaft 290.

In assembly, operation and use, spinal implant system 10, similar to the systems and methods described herein, includes an automated, intra-operative system configured to contour spinal rod 200 with pedicle screws to form a corrective spinal construct 202, as shown in FIGS. 37-41.

In use, to treat the affected section of vertebrae, a medical practitioner obtains access to a surgical site including vertebrae in any appropriate manner, such as through incision and retraction of tissues. Spinal implant system 10 may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. Spinal implant system 10 is then employed to augment the surgical treatment.

During the surgical procedure, computer 14 receives data from a template, as described herein. The template is employed in-situ and/or intra-operatively during the procedure and/or can be transferred from a sterile surgical field for analysis to define a selected spinal rod contour or configuration of spinal rod 200.

For example, digitizer 450, as described herein, is directly connected to a bone fastener 600 attached with vertebra of vertebral level V1 to capture and/or identify selected data points corresponding to receivers 602 of bone fasteners 600 selectively disposed along vertebrae V to generate three dimensional coordinates of a selected implant configuration of spinal rod 200, as shown in FIG. 37. Base 460 is disposed in a selected orientation relative to bone fastener 600 disposed at vertebral level V1 and/or vertebrae V, and fixed with receiver 602, as described herein, to provide a reference for intra-operative identification of coordinates of bone fasteners 600 connected with vertebral levels of vertebrae V relative to vertebral level V1.

Arm 452 is articulated to orient tip 454 such that end effector 456 is engageable with receivers 602, as described herein. The position sensors of digitizer 450 intra-operatively measure, sample, capture and/or identify selected positional data points of end effector 456 in three dimensional space corresponding to receivers 602 and positioning of bone fasteners 600 to determine a selected spinal rod curvature of spinal rod 200 along vertebrae V. The data points include three dimensional coordinates of a selected spinal rod configuration, which are communicated to computer 14 and converted into a three dimensional model of spinal rod 200, as described herein. The three dimensional model of spinal rod 200 is translated into machine code and communicated to implant bending device 24 within a sterile field to contour spinal rod 200. A digitized image of spinal rod 200 is displayed from monitor 15, as described herein.

For example, upon collection and/or acquisition of data corresponding to the template, as described herein, three dimensional coordinates of the selected implant configuration of spinal rod 200 are generated. The coordinates of the selected implant configuration are communicated to computer 14 and transferred to implant bending device 24 and/or displayed from a graphical interface, as described herein.

Implant bending device 24 is utilized intra-operatively in a sterile environment. Container 40 is covered by a sterile drape 500. Carrier 20, mandrel 26 and arm 28 perforate drape 500 to facilitate movement and bending of spinal rod 200. Carrier 20, mandrel 26 and arm 28 are configured for disinfection by an autoclave.

Spinal rod 200 is connected with implant bending device 24. An end of spinal rod 200 is engaged with part 98. An end of spinal rod 200 is disposed within passageway P. Carrier 20 is actuated to axially translate spinal rod 200 relative to mandrel 26 and arm 28. Spinal rod 200 translates along surface 252. Surface 320 of arm 28 is rotated into engagement with spinal rod 200 to bend arm to a desired angle.

Based on the three dimensional coordinates of the selected implant configuration of spinal rod 200 communicated to computer 14 and transferred to implant bending device 24, arm 28 reacts to signals from computer 14 to manipulate and/or bend spinal rod 200 to the selected implant configuration. In operation, contact sensor 30 determines or senses an initial contact point or engagement of arm 28 with spinal rod 200, as described herein, which can represent a "0" degree reference position, by rotating arm 28 in increments, for example, increments of 0.5 angular degrees. Contact sensor 30 sends signals to computer 14 to indicate the "0" degree reference position, which can be displayed from a graphical interface, as described herein.

For example, if a selected curvature of spinal rod 200 includes a 35 degree bend, arm 28 rotates 35 degrees in a first direction, as shown by arrow A in FIG. 35, relative to the "0" degree reference position and engages spinal rod 200 to effect a 35 degree bend. Arm 28 is then rotated in a second opposite direction, as shown by arrow B in FIG. 35, in increments, for example, of 0.5 angular degrees to disengage arm 28 from spinal rod 200. When arm 28 no longer has contact with spinal rod 200, as detected by contact sensor 30 and described herein, the resulting bend formed in spinal rod 200 is measured based on arm 28 position and/or angle relative to the "0" degree reference position detected by contact sensor 30. Contact sensor 30 sends signals to computer 14 to indicate the position of the resulting bend angle, which can be displayed from a graphical interface. The difference between the resulting bend angle and the selected curvature of spinal rod 200 of 35 degrees represents spring back, which can include a delta angle measured by arm 28 position, which can be displayed from a graphical interface. Computer 14 sends signals to implant bending device 24 such that arm 28 re-engages spinal rod 200 for further bending operation to facilitate compensation for spring back to effect the 35 degree bend. In some embodiments, contact sensor 30 can be employed with storage media of computer 14 to create a lookup table to facilitate compensation for spring back. In some embodiments, contact sensor 30 facilitates bending spinal rod 200 to a selected curvature, measuring spring back and bending spinal rod 200 to a new angle with spring back compensation. In some embodiments, arm 28 has a torque application capacity of one or more values in a range of 70-85 N-m on spinal rod 200.

Spinal rod 200, contoured to the selected implant configuration via implant bending device 24, is attached with vertebrae V via bone fasteners 600, as shown in FIG. 41, to form spinal construct 202 for treating a spine disorder. Upon completion of the procedure, the surgical instruments, assemblies and non-implanted components of spinal implant system 10 are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
   a spinal implant template including a base configured to be connected to vertebral tissue and a member movable relative to the base, the member including a sensor configured to identify coordinates of one or more bone fasteners configured to be connected with the vertebral tissue; and
   an implant bending device including work surfaces engageable with a spinal implant to manipulate the spinal implant to a selected implant configuration based on the coordinates,
   wherein the base includes a spheroidal joint comprising a socket and a ball having a post extending therefrom, the post including a mating part engageable with a receiver of a bone fastener configured to be connected with vertebrae.

2. A spinal implant system as recited in claim 1, wherein the member is connected with the base by a joint that is rotatable relative to the base.

3. A spinal implant system as recited in claim 1, wherein the base includes a rotation sensor.

4. A spinal implant system as recited in claim 1, wherein the base is movable relative to the receiver in a plurality of axial orientations.

5. A spinal implant system as recited in claim 1, wherein the base includes a lock that fixes orientation of the base relative to the receiver.

6. A spinal implant system as recited in claim 1, wherein the member includes an articulated arm.

7. A spinal implant system as recited in claim 1, wherein the member includes an articulating arm having a spherical tip disposable with receivers of the one or more bone fasteners configured to be connected with one or more vertebral levels.

8. A spinal implant system as recited in claim 1, wherein the spinal implant template comprises a digitizer that intra-operatively identifies the coordinates and communicates with a computer to display the coordinates from a graphical interface that provides implant indicia.

9. A spinal implant system as recited in claim 1, wherein the sensor intra-operatively identifies the coordinates and communicates with a computer having a graphical interface that provides implant indicia.

10. A spinal implant system as recited in claim 9, wherein implant bending device includes an intra-operative, sterilized container for disposal of the work surfaces.

11. A spinal implant system as recited in claim 1, further comprising an implant contact sensor connected with the work surfaces and being configured to detect contact of at least one of the work surfaces with the spinal implant.

12. A spinal implant system comprising:
   a control device including a digitizer configured to be connected to a first vertebral level, the digitizer being configured to intra-operatively identify coordinates of one or more bone fasteners configured to be connected with vertebral levels relative to the first vertebral level, the digitizer communicating with a computer to display the coordinates from a graphical interface;
   a displacement module that communicates with the control device and includes a movable support connectable with a spinal implant; and
   a bending module that communicates with the control device and includes work surfaces engageable with the spinal implant to manipulate the spinal implant to a selected implant configuration based on the coordinates,
   wherein the digitizer includes a base including a spheroidal joint comprising a socket and a ball having a post extending therefrom, the post including a mating part engageable with a receiver of a bone fastener configured to be connected with the first vertebral level such that the post is rotatable relative to the receiver in a plurality of axial orientations.

13. A spinal implant system as recited in claim 12, wherein the digitizer includes an articulating arm that is movable relative to the base, the articulating arm having a spherical tip disposable with receivers of the one or more bone fasteners configured to be connected with the vertebral levels.

14. A spinal implant system as recited in claim 12, wherein the digitizer includes a lock that fixes orientation of the digitizer relative to the bone fastener configured to be connected with the first vertebral level.

15. A spinal implant system as recited in claim 12, wherein the bending module is mounted with an intra-operative, sterilized container for disposal of the work surfaces.

16. A spinal implant system as recited in claim 12, further comprising an implant contact sensor connected with the work surfaces and being configured to detect contact of at least one of the work surfaces with the spinal implant.

17. A spinal implant system comprising:
   a first bone fastener comprising a receiver having a first mating part;
   a connector comprising a post having a second mating part engageable with the first mating part to couple the post to the receiver, the connector comprising a ball extending from the post;
   a spinal implant template including a base defining a socket and a member movable relative to the base, the ball being disposed in the socket to define a spheroidal joint, the member including a sensor configured to identify coordinates of one or more second bone fasteners; and
   an implant bending device including work surfaces engageable with a spinal implant to manipulate the spinal implant to a selected implant configuration based on the coordinates.

18. A spinal implant system as recited in claim 17, wherein the mating parts are threads.

19. A spinal implant system as recited in claim 17, wherein the member includes an articulating arm.

20. A spinal implant system as recited in claim 19, wherein the articulating arm has a spherical tip disposable with receivers of the second bone fasteners.

* * * * *